US012127767B2

(12) United States Patent
Vedula et al.

(10) Patent No.: US 12,127,767 B2
(45) Date of Patent: *Oct. 29, 2024

(54) UNIPLANAR BONE SCREW

(71) Applicant: Zimmer Spine, Inc., Edina, MN (US)

(72) Inventors: Krishna C Vedula, Chanhassen, MN (US); Hugh Hestad, Edina, MN (US); Jason Piehl, Apple Valley, MN (US); David Nuckley, Minneapolis, MN (US); Jeremy Lemoine, Leander, TX (US)

(73) Assignee: Zimmer Spine, Inc., Edina, MN (US)

(*) Notice: Subject to any disclaimer, the term of this patent is extended or adjusted under 35 U.S.C. 154(b) by 210 days.

This patent is subject to a terminal disclaimer.

(21) Appl. No.: 17/218,474

(22) Filed: Mar. 31, 2021

(65) Prior Publication Data

US 2021/0212731 A1 Jul. 15, 2021

Related U.S. Application Data

(63) Continuation of application No. 16/160,607, filed on Oct. 15, 2018, now Pat. No. 10,987,139, which is a continuation of application No. 15/404,927, filed on Jan. 12, 2017, now Pat. No. 10,130,396, which is a continuation of application No. 14/243,992, filed on Apr. 3, 2014, now Pat. No. 9,549,765.

(51) Int. Cl.
*A61B 17/70* (2006.01)
*A61B 17/86* (2006.01)

(52) U.S. Cl.
CPC .......... *A61B 17/7038* (2013.01); *A61B 17/70* (2013.01); *A61B 17/7032* (2013.01); *A61B 17/8625* (2013.01)

(58) Field of Classification Search
CPC . A61B 17/70; A61B 17/7038; A61B 17/7032; A61B 17/86; A61B 17/8625
See application file for complete search history.

(56) References Cited

U.S. PATENT DOCUMENTS

| | | |
|---|---|---|
| 5,989,254 A | 11/1999 | Katz |
| 6,520,963 B1 | 2/2003 | Mckinley |
| 6,981,973 B2 | 1/2006 | Mckinley |
| 7,691,129 B2 | 4/2010 | Felix |
| 7,749,258 B2 | 7/2010 | Biedermann et al. |
| 7,892,259 B2 | 2/2011 | Biedermann et al. |

(Continued)

FOREIGN PATENT DOCUMENTS

| | | |
|---|---|---|
| DE | 202012105062 U1 | 1/2013 |
| WO | WO-2008119006 A1 | 10/2008 |

(Continued)

OTHER PUBLICATIONS

U.S. Appl. No. 14/243,992 U.S. Pat. No. 9,549,765, filed Apr. 3, 2014, Uniplanar Bone Screw.
U.S. Appl. No. 15/404,927 U.S. Pat. No. 10,130,396, filed Jan. 12, 2017, Uniplanar Bone Screw.
U.S. Appl. No. 16/160,607, filed Oct. 15, 2018, Uniplanar Bone Screw.

(Continued)

*Primary Examiner* — Christopher J Beccia
(74) *Attorney, Agent, or Firm* — Sheridan Ross P.C.

(57) ABSTRACT

A uniplanar bone anchor including a housing and a bone screw is provided. The lower region of the housing defines mating elements that mate with engaging elements on the bone screw to limit movement of the housing relative to the bone screw to a single plane.

20 Claims, 28 Drawing Sheets

(56) References Cited

U.S. PATENT DOCUMENTS

| | | | |
|---|---|---|---|
| 7,922,748 B2 | 4/2011 | Hoffman | |
| 7,942,909 B2 | 5/2011 | Hammill, Sr. et al. | |
| 7,942,910 B2 | 5/2011 | Doubler et al. | |
| 7,942,911 B2 | 5/2011 | Doubler et al. | |
| 7,951,172 B2* | 5/2011 | Chao | A61B 17/7038 606/265 |
| 8,048,133 B2 | 11/2011 | Biedermann et al. | |
| 8,197,518 B2 | 6/2012 | Hammill, Sr. et al. | |
| 8,382,805 B2 | 2/2013 | Wang et al. | |
| 8,419,778 B2 | 4/2013 | Barry | |
| 9,549,765 B2 | 1/2017 | Vedula et al. | |
| 10,130,396 B2 | 11/2018 | Vedula et al. | |
| 10,987,139 B2* | 4/2021 | Vedula | A61B 17/8625 |
| 2006/0155277 A1 | 7/2006 | Metz-stavenhagen | |
| 2006/0200131 A1 | 9/2006 | Chao et al. | |
| 2007/0090238 A1 | 4/2007 | Justis | |
| 2007/0161996 A1 | 7/2007 | Biedermann et al. | |
| 2008/0147129 A1 | 6/2008 | Biedermann et al. | |
| 2009/0076552 A1 | 3/2009 | Tornier | |
| 2009/0105769 A1 | 4/2009 | Rock et al. | |
| 2009/0105770 A1 | 4/2009 | Berrevoets et al. | |
| 2009/0198280 A1 | 8/2009 | Spratt et al. | |
| 2010/0318135 A1 | 12/2010 | Biedermann et al. | |
| 2011/0009911 A1 | 1/2011 | Hammill, Sr. et al. | |
| 2011/0040336 A1 | 2/2011 | Hammill, Sr. et al. | |
| 2011/0106173 A1* | 5/2011 | Lindemann | A61B 17/7038 606/305 |
| 2011/0112585 A1 | 5/2011 | Biedermann et al. | |
| 2011/0178558 A1 | 7/2011 | Barry | |
| 2011/0178559 A1 | 7/2011 | Barry | |
| 2011/0208251 A1 | 8/2011 | Hammill, Sr. et al. | |
| 2012/0109224 A1 | 5/2012 | Biedermann | |
| 2012/0123486 A1 | 5/2012 | Werner | |
| 2012/0232598 A1* | 9/2012 | Hestad | A61B 17/7037 29/446 |
| 2012/0330364 A1 | 12/2012 | Jacofsky et al. | |
| 2013/0023935 A1 | 1/2013 | Pham et al. | |
| 2013/0096622 A1 | 4/2013 | Biedermann et al. | |
| 2013/0096624 A1* | 4/2013 | Di Lauro | A61B 17/7011 606/279 |
| 2015/0282844 A1 | 10/2015 | Vedula et al. | |
| 2017/0189075 A1 | 7/2017 | Vedula et al. | |
| 2019/0046242 A1 | 2/2019 | Vedula et al. | |

FOREIGN PATENT DOCUMENTS

| | | |
|---|---|---|
| WO | WO-2013063469 A1 | 5/2013 |
| WO | WO-2015153418 A2 | 10/2015 |
| WO | WO-2015153418 A3 | 10/2015 |

OTHER PUBLICATIONS

"U.S. Appl. No. 14/243,992, Non Final Office Action mailed Apr. 27, 2016", 9 pgs.

"U.S. Appl. No. 14/243,992, Notice of Allowance mailed Sep. 13, 2016", 5 pgs.

"U.S. Appl. No. 14/243,992, Preliminary Amendment filed Jun. 17, 2015", 6 pgs.

"U.S. Appl. No. 14/243,992, Response filed Aug. 25, 2016 to Non Final Office Action mailed Apr. 27, 2016", 11 pgs.

"U.S. Appl. No. 15/404,927, Final Office Action mailed Nov. 24, 2017", 10 pgs.

"U.S. Appl. No. 15/404,927, Non Final Office Action mailed Jul. 25, 2017", 9 pgs.

"U.S. Appl. No. 15/404,927, Notice of Allowance mailed Jul. 18, 2018", 6 pgs.

"U.S. Appl. No. 15/404,927, Preliminary Amendment filed Apr. 19, 2017", 7 pgs.

"U.S. Appl. No. 15/404,927, Response filed Feb. 26, 2018 to Final Office Action mailed Nov. 24, 2017", 12 pgs.

"U.S. Appl. No. 15/404,927, Response filed Oct. 25, 2017 to Non Final Office Action mailed Jul. 25, 2017", 11 pgs.

"Application Serial No. 15715621.7, Response filed May 25, 17 to action mailed on Nov. 15, 2017", 17 pgs.

"U.S. Appl. No. 16/160,607, Non Final Office Action mailed Sep. 11, 2020", 9 pgs.

"U.S. Appl. No. 16/160,607, Notice of Allowance mailed Jan. 6, 2021", 6 pgs.

"U.S. Appl. No. 16/160,607, Preliminary Amendment filed Jan. 10, 2019", 7 pgs.

"U.S. Appl. No. 16/160,607, Response filed Aug. 24, 2020 to Restriction Requirement mailed Jun. 29, 2020", 7 pgs.

"U.S. Appl. No. 16/160,607, Response filed Dec. 8, 2020 to Non Final Office Action mailed Sep. 11, 2020", 9 pgs.

"U.S. Appl. No. 16/160,607, Restriction Requirement mailed Jun. 29, 2020", 5 pgs.

"International Application Serial No. PCT/US2015/023272, International Preliminary Report on Patentability mailed Oct. 13, 2016", 9 pgs.

"International Application Serial No. PCT/US2015/023272, International Search Report mailed Oct. 8, 2015", 6 pgs.

"International Application Serial No. PCT/US2015/023272, Invitation to Pay Add'l Fees and Partial Search Rpt mailed Aug. 21, 2015", 5 pgs.

"International Application Serial No. PCT/US2015/023272, Written Opinion mailed Oct. 8, 2015", 7 pgs.

* cited by examiner

UNIPLANAR BONE SCREW

CROSS REFERENCE TO RELATED APPLICATION

The present application is a continuation of U.S. patent application Ser. No. 16/160,607, filed Oct. 15, 2018, now U.S. Pat. No. 10,987,139, which is a continuation of U.S. patent application Ser. No. 15/404,927, filed Jan. 12, 2017, now U.S. Pat. No. 10,130,396, which is a continuation of U.S. patent application Ser. No. 14/243,992, filed Apr. 3, 2014, now U.S. Pat. No. 9,549,765, all of which are incorporated herein by this reference in their entirety.

TECHNICAL FIELD

The disclosure is directed to vertebral anchors for use with orthopedic fixation systems. More particularly, the disclosure is directed to uniplanar bone anchors.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

In some cases, it may be desirable to use an anchor that provides a range of motion in only one plane.

SUMMARY

The disclosure is directed to several alternative designs, materials and methods of assembling uniplanar bone anchor structures and assemblies.

In one example, a uniplanar bone anchor may include a housing and a bone screw, where the housing has a bore with a longitudinal axis, the bore extending through the housing to a lower opening, the housing including a channel for receiving an elongate member, the channel extending transverse to the bore. The bone screw may have a longitudinal axis and may include a head and a shank extending from the head, the bone screw may be configured to extend through the bore with the head positionable in the housing and the shank extending from the lower opening of the housing, the head having a substantially spherical surface with planar surfaces on opposing sides of the head. The housing may include at least one mating element extending from an inner surface of the housing into the bore, transverse to the longitudinal axis of the housing, the at least one mating element configured to couple with the planar surfaces on the screw head such that the bone screw is moveable relative to the housing with the longitudinal axis of the bone screw being positionable in any one of a plurality of angular positions within a single plane relative to the longitudinal axis of the bore.

In some examples, the mating element may be a single element and may include two opposing planar surfaces extending parallel to the longitudinal axis of the housing. The mating element may extend into the bore along an entire circumference of the inner surface of the housing, and an opening in the mating element may define the planar surfaces. In some examples, the opposing planar surfaces may be separated by opposing curved surfaces.

In another example, bone anchor may include a housing having a bore extending therethrough defining an inner surface and a channel extending transverse to the bore, and a mating element extending from an inner surface of the housing into the bore, the mating element including opposing planar surfaces, and a bone screw including a head and a shank extending from the head, the screw positionable within the housing such that the screw head resides in the housing and the shaft extends outside the housing, the screw head having a spherical surface with opposing planar surfaces configured to mate with the opposing planar surfaces of the housing, wherein mating of the opposing planar surfaces on the screw head and the housing results in uniplanar movement of the housing relative to the bone screw, the inner surface of the housing including curved surfaces capable of slidably coupling with the spherical surface of the bone screw head, wherein the inner surface of at least a lower end of the housing includes threading extending across the curved surfaces and the opposing planar surfaces.

In another example, a bone anchor may include a housing having a bore extending through the housing from an upper end to a lower end, the housing having a channel extending transverse to the bore, the housing including at least one mating element, and a bone screw including a head and a shank extending from the head, the head positionable within the housing, the head having at least one engaging element configured to mate with the at least one mating element on the housing to limit motion of the bone screw relative to the housing to a single plane, and an inner surface of at least the lower end of the housing may include threading.

The above summary of some examples is not intended to describe each disclosed example or every implementation of the invention.

BRIEF DESCRIPTION OF THE DRAWINGS

The invention may be more completely understood in consideration of the following detailed description of various examples in connection with the accompanying drawings, in which.

Figure 1:
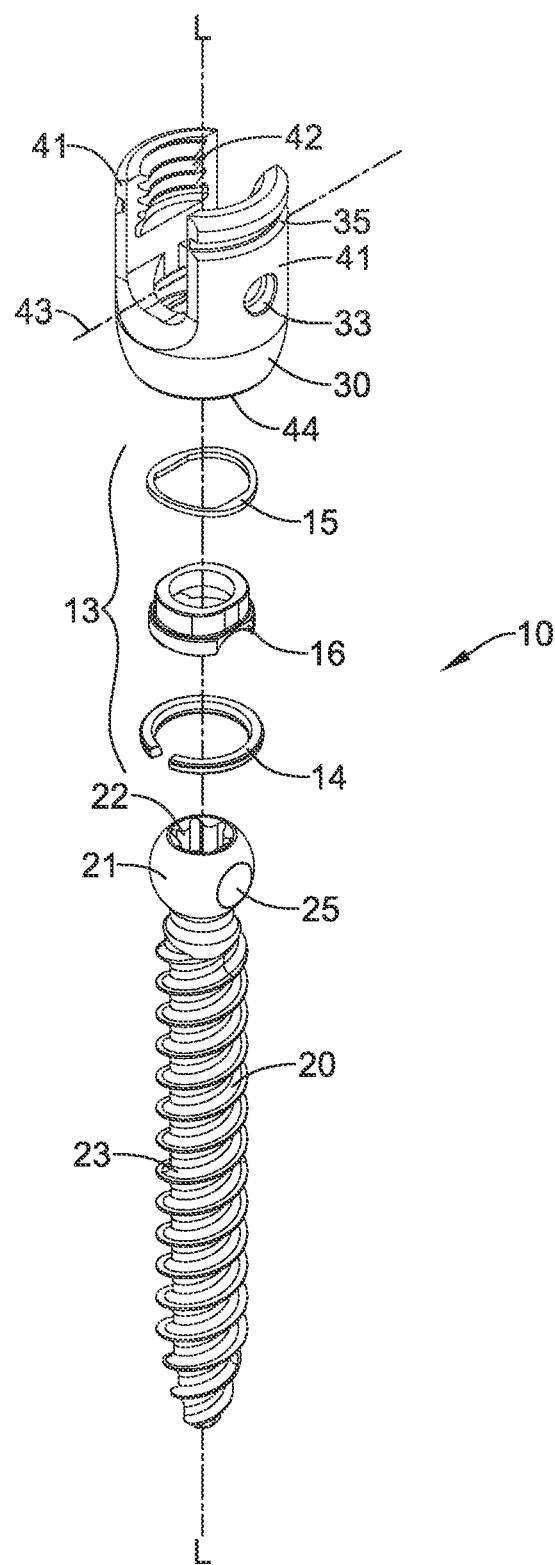
FIG. 1 is a perspective exploded view of components of an exemplary bone anchor.

While the invention is amenable to various modifications and alternative forms, specifics thereof have been shown by way of example in the drawings and will be described in detail. It should be understood, however, that the intention is not to limit aspects of the invention to the particular examples described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification, the term "top" refers to the portion of the figure or element closer the top of the page, and the term "bottom" refers to the portion of the figure or element closer to the bottom of the page.

The following detailed description should be read with reference to the drawings in which similar elements in different drawings are numbered the same. The detailed description and the drawings, which are not necessarily to scale, depict illustrative examples and are not intended to limit the scope of the invention. The illustrative examples depicted are intended only as exemplary. Selected features of any illustrative example may be incorporated into an additional example unless clearly stated to the contrary.

A uniplanar bone anchor allows for movement of a housing relative to a bone screw in only a single plane. Structural elements on the screw head and the interior of the housing may provide the uniplanar movement. The screw may be bottom loading or top loading. FIGS. 1-8 illustrate a bottom loading bone screw, FIGS. 9-17 illustrate a first example of a top loading bone screw, FIGS. 18-23 illustrate a second example of a top loading bone screw, and FIGS. 24-28 illustrate a third example of a top loading bone screw.

FIG. 1 is an exploded view illustrating components of an exemplary bone anchor 10. The bone anchor 10 may include a housing 30, a bone screw 20, and a retainer assembly 13. Bone anchor 10 may be referred to as a bottom loading system, with the bone screw 20 inserted through the bottom of the housing 30. In use, the bone anchor 10, which may be screwed into a vertebra, may serve to couple a rod or other elongate member (not shown) extending along a portion of a spinal column. The rod or elongate member may fit into a U-shaped channel 43 formed by opposing arms 41 of the housing 30. The channel 43 may extend along a transverse or horizontal axis. The bone anchor 10 may include particular degrees of adjustability within a single plane, ensuring that, when multiple bone anchors are used with a single rod, each screw may be locked down at the particular locations and orientations desired by the practitioner, and the housings may be adjusted to a desired position within the single plane to receive the rod.

Figure 6:
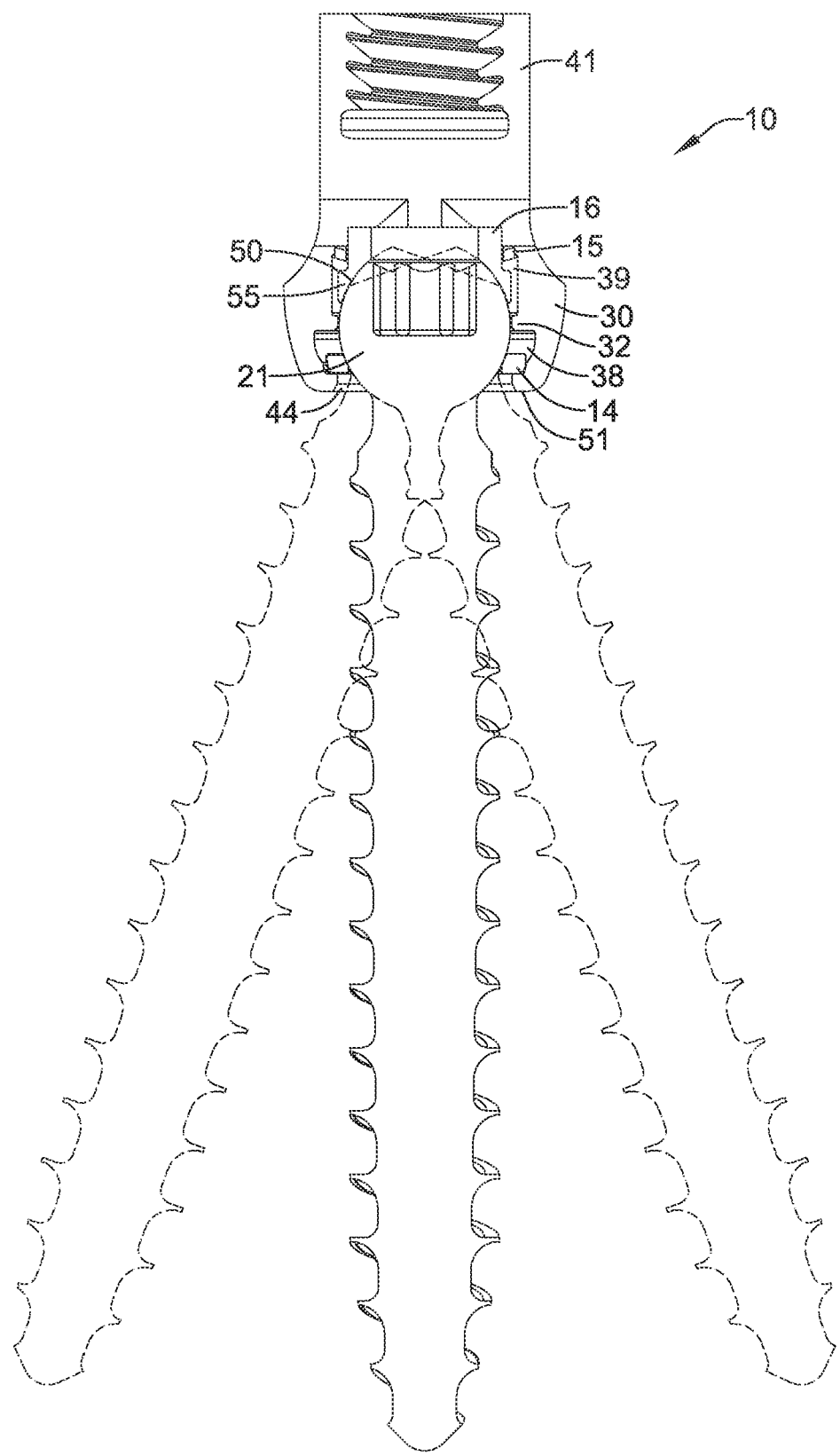
FIG. 6 is a cross-sectional view of the assembled anchor of FIG. 1, with phantom lines showing alternate positions of the screw.

It should be noted that in practice, even though the screw 20 may be first screwed into the vertebra, then the housing 30 may be adjusted to accommodate a rod in the U-shaped channel 43, in this document we examine the elements from the point of view of the housing 30, so that the screw 20 may be referred to as being adjustable with respect to the housing 30. The housing has a longitudinal axis L-L as seen in FIG. 1, which may be considered to be a vertical axis. A transverse or horizontal axis along which the channel 43 lies may extend transverse to the longitudinal axis L-L. The longitudinal axis L-L bisects a vertical plane. The screw 20 may be moveable relative to the housing 30 with the longitudinal axis of the screw 20 being positionable in any one of a plurality of angular positions within the vertical plane relative to the longitudinal axis of the housing bore, as seen in FIG. 6. The screw 20 and housing 30 may thus be moveable relative to each other in a single plane. The screw 120, 220, 320 and housing 130, 230, 330 shown in FIGS. 9-28 also exhibit uniplanar movement.

Figure 2:
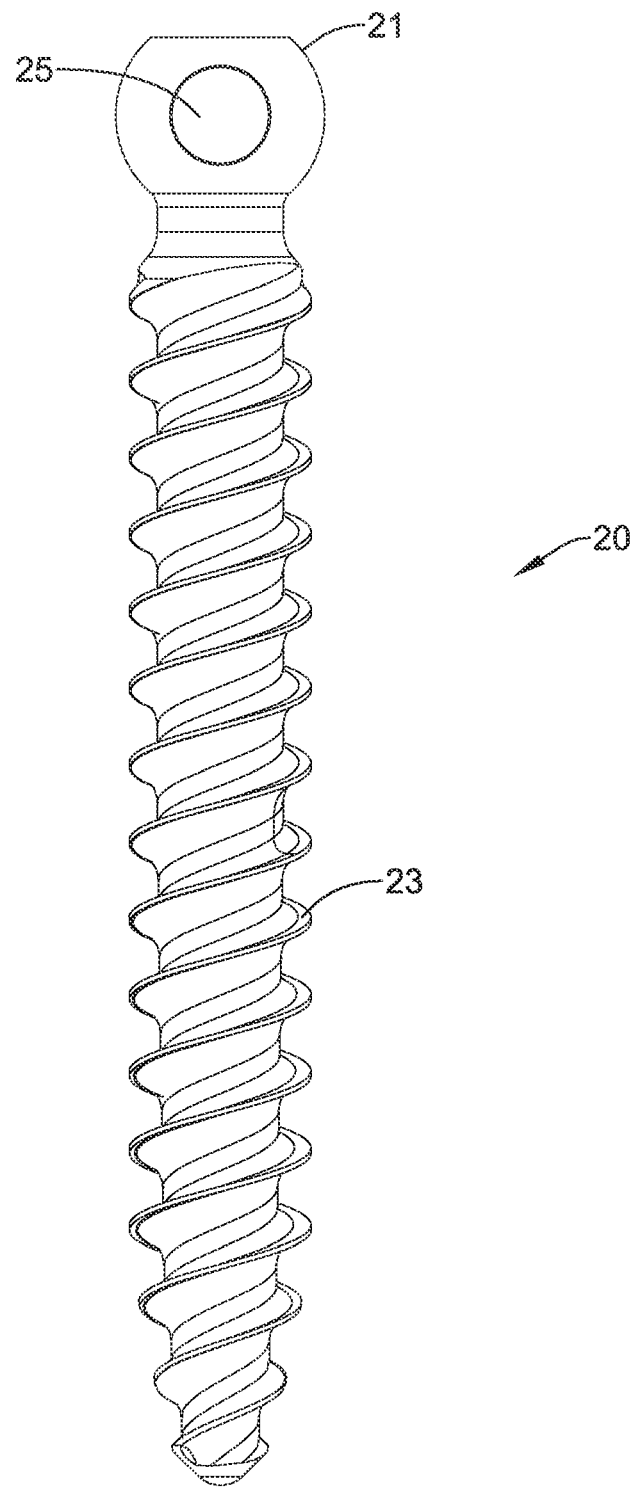
FIG. 2 is a side view of the bone screw of FIG. 1.
Figure 3:
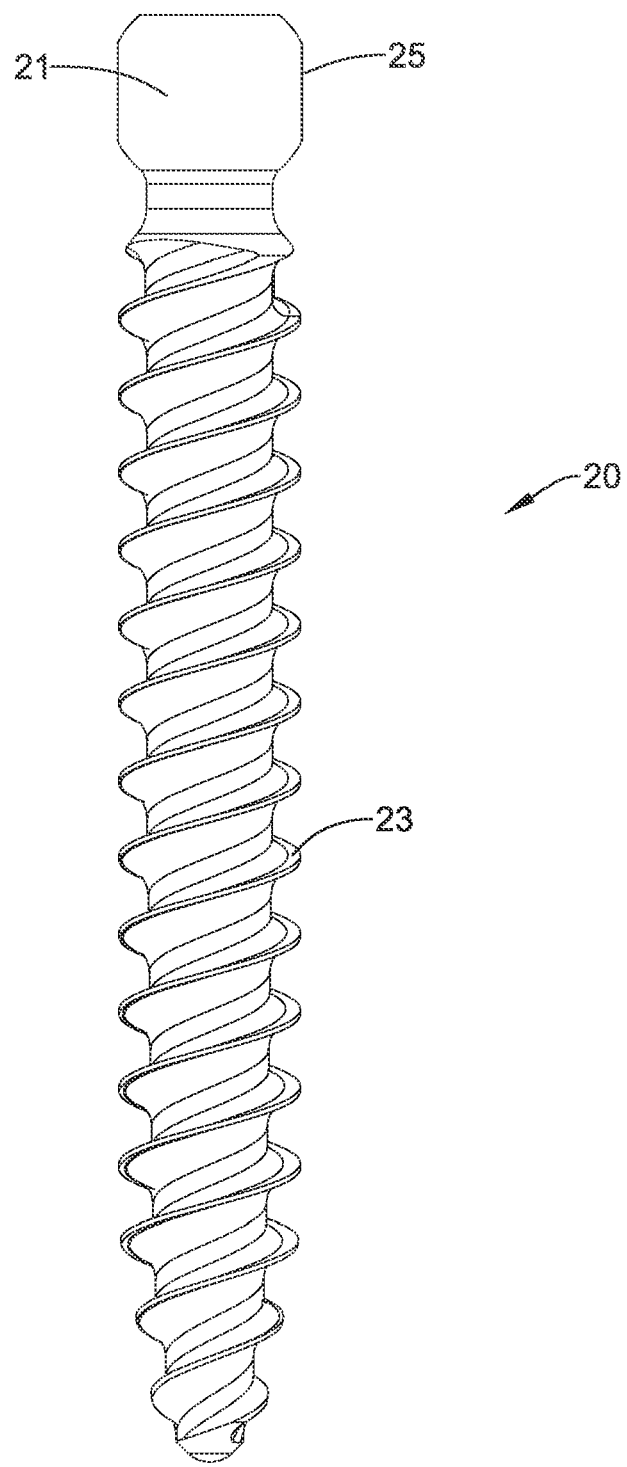
FIG. 3 is a side view of the bone screw of FIG. 1 transverse to the view of FIG. 2.

As shown in FIGS. 1-3, the screw 20 may have a threaded shank 23 configured to extend out the bottom opening of the housing 30 and engage a vertebra. The screw 20 may be a monolithic, single piece structure having a longitudinal axis L-L, as shown in FIG. 1. The screw 20 may have a head 21 that is generally spherical in shape with opposing planar surfaces 25 and a driver interface such as a keyed portion 22. The structure of the housing 30 and retainer assembly 13 in combination with the planar surfaces 25 on the screw head 21 may allow pivoting of the screw head 21 in a single plane with respect to the housing 30.

Figure 5:
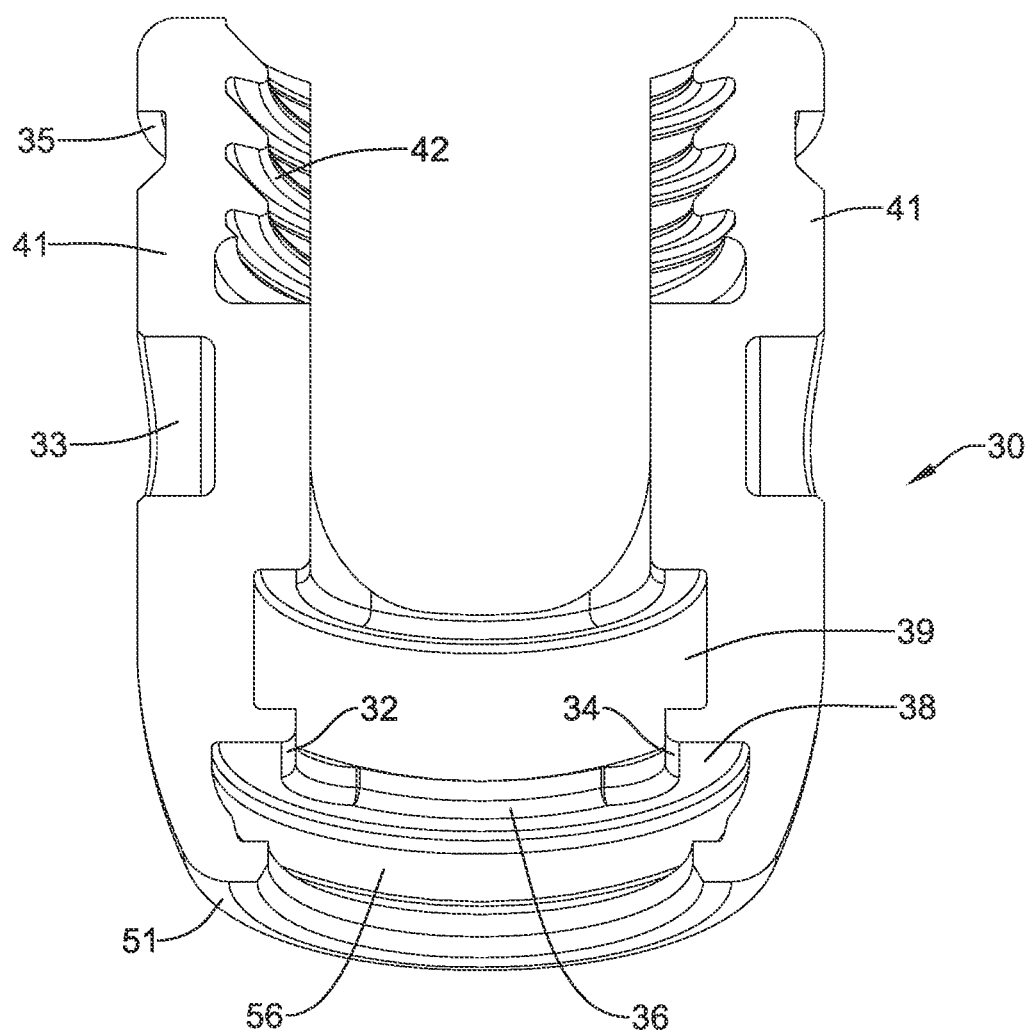
FIG. 5 is a cross-sectional partially elevated view of the housing of the anchor of FIG. 1.

As seen in FIG. 5, the housing 30 may be monolithic, thus formed as a single piece. In other examples the housing 30 may be formed of multiple pieces that are connected prior to use. The housing 30 may have a bore 44 extending through the housing 30 along the longitudinal axis L-L of the housing, transverse to the U-shaped channel 43. The screw 20 may be received in the bore 44. Threading 42 may be provided on the inner surface of the arms 41 for connection with a fastener or set screw (not shown). The housing 30 may include additional features such as recesses 33 or grooves 35 for interaction with insertion tools, extension sleeves, reduction tools, etc. The housing 30 may have a generally circular opening 56 in the bottom surface 51 of the housing, with the opening 56 sized and shaped to receive the screw head 21 for bottom loading.

Figure 7:
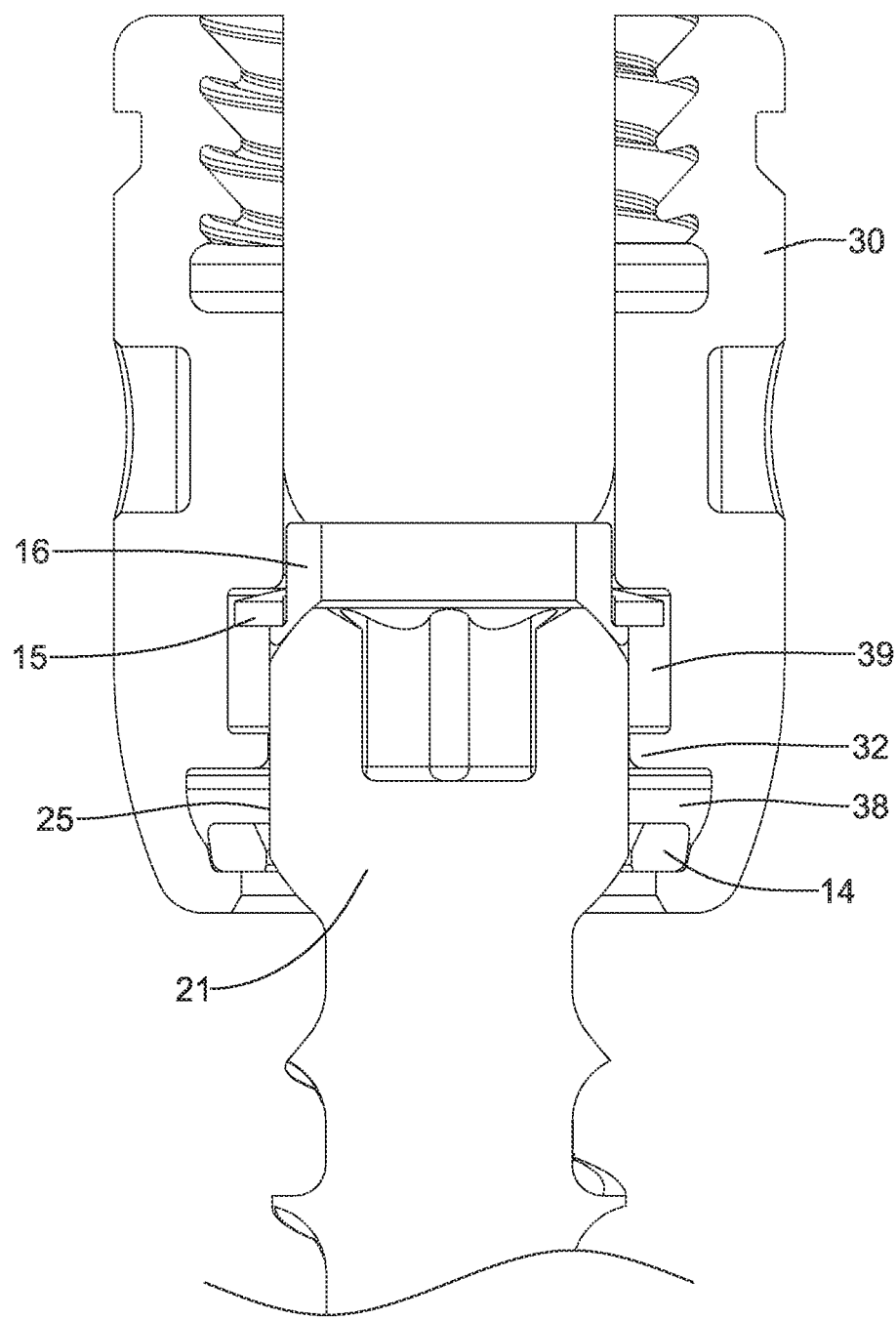
FIG. 7 is a cross-sectional view of the assembled anchor of FIG. 1 transverse to the cross-sectional view of FIG. 6.

The housing 30 may include a mating element 32 such as one or more protrusion extending from an inner wall of the housing 30 into the bore 44, transverse to the longitudinal axis L-L of the housing. The mating element 32 may include a single mating element extending into the bore 44 along an entire circumference of the inner surface of the housing 30, with an opening defining opposing planar surfaces 34 and opposing curved surfaces 36, as shown in FIGS. 5-7. The curved surfaces 36 may be configured to mate with the spherical surface of the screw head 21, and the planar surfaces 34 may be configured to mate with the planar surfaces 25 of the screw head 21. In some examples, the mating element 32 may include discrete portions extending from an inner wall of the housing 30 into the bore 44 (not shown). The mating element 32 may at least partially define a lower chamber 38 and an upper chamber 39 within the housing 30. The screw head 21 may be received within the housing 30 in a first orientation or a second orientation, turned 180 degrees from the first orientation. The mating of the planar surfaces 34 of the housing with the planar surfaces 25 of the screw head 21 may prevent rotation of the screw 20 around the longitudinal axis L-L. The mating of the curved surfaces 36 of the housing with the spherical surface of the screw head 21 may allow movement of the screw head 21 within a single plane. As shown in phantom in FIG. 6, the screw 20 may be moved within a single plane to various positions relative to the housing 30.

The head 21 of the screw 20 may be held in place by a retainer assembly 13, which may prevent the screw 20 from being removed through the bottom of the housing 30 once the screw is inserted. The retainer assembly 13 may be in the form of one or more rings having a central aperture, which may allow the practitioner to insert a screwdriver through the aperture of the rings to engage a driver interface such as a keyed portion 22 on the head 21 of the screw 20. The retainer assembly 13 may include a retaining ring 14, a wave washer or biasing member 15, and an insert 16. The exemplary retainer assembly 13 in FIG. 1 includes an insert 16 that may contact the head 21 of the screw 20, a biasing member 15, and a retaining ring 14. The retaining ring 14 may be a split ring, as shown in FIG. 1, or it may be a continuous ring. The biasing member 15 may be a wave washer. The retaining ring 14 may be received in the lower chamber 38 of the housing 30, below the mating element 32. The retaining ring 14 may contact a lower surface of the screw head 21, and may prevent the screw 20 from exiting the housing 30 through the lower opening of the housing 30, as shown in FIG. 6.

Figure 4:
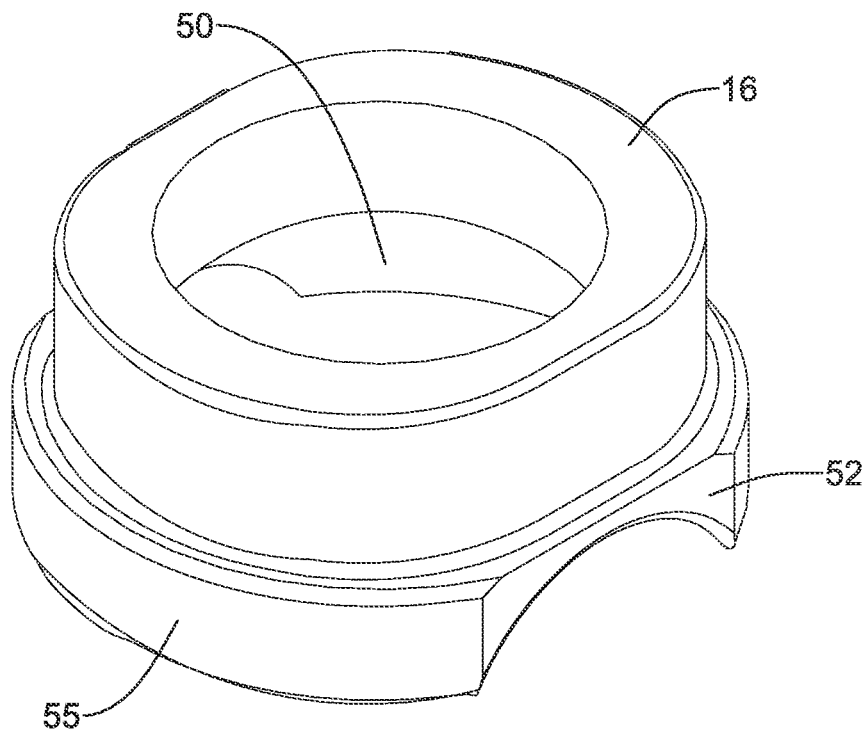
FIG. 4 is a perspective view of the insert of the apparatus of FIG. 1.
Figure 8:
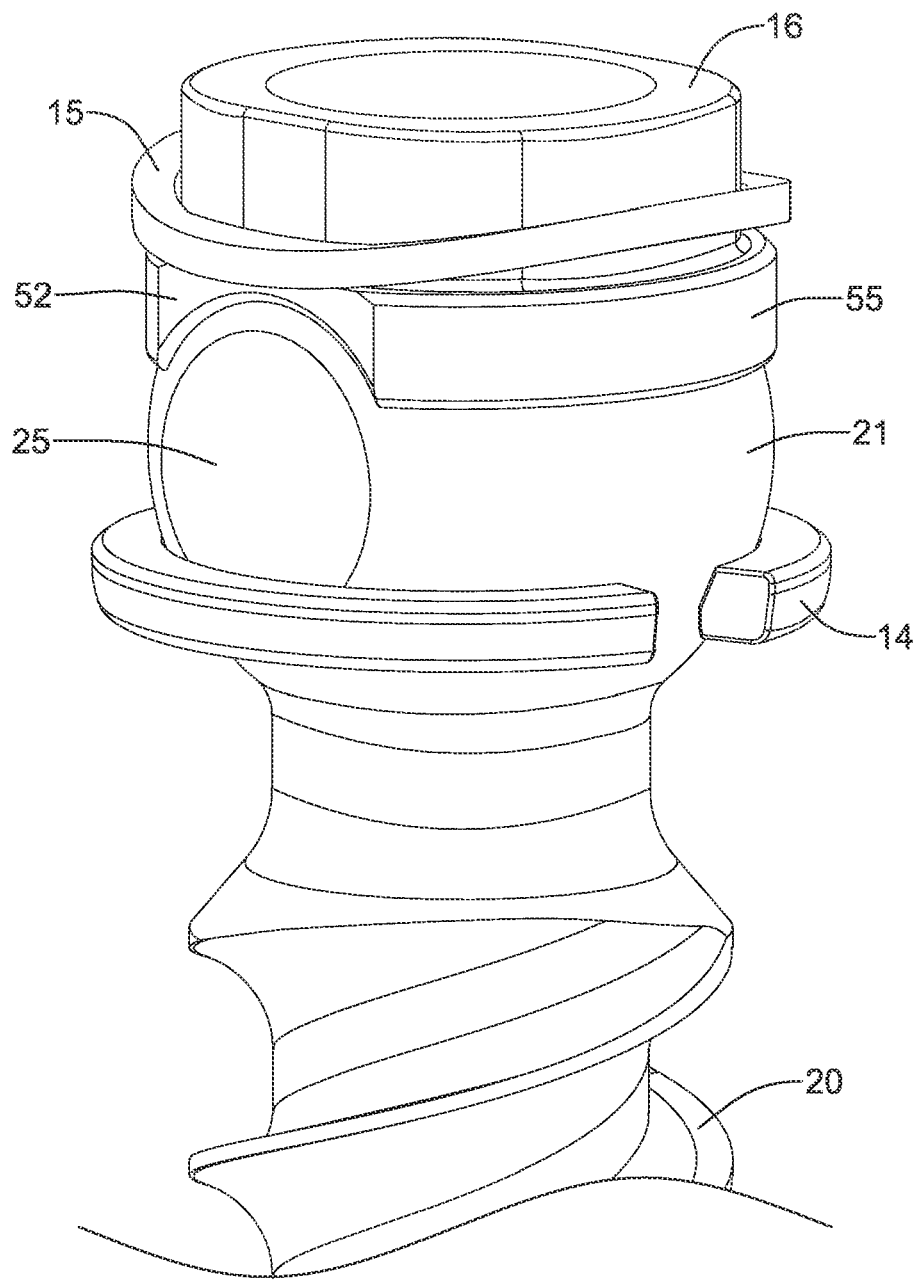
FIG. 8 is a perspective view of the assembled bone anchor of FIG. 1, without the housing.

As seen in FIGS. 4 and 6, the insert 16 may include a concave inner annular surface 50 that has a radius of curvature matched to that of the screw head 21, so that when the housing 30 is pivoted relative to the screw 20, it may remain held in place by the insert 16. The insert 16 may have opposing planar surfaces 52 that, when aligned with the planar surfaces 25 of the screw head 21, as shown in FIG. 8, may allow the screw head 21 and insert 16 to fit within the interior of the housing 30. The insert 16 may have a lower lip 55 that extends from the insert 16 into the upper chamber 39 when the insert 16 is disposed on the screw 20 within the housing 30. The biasing member 15 may be placed over the insert 16 such that the biasing member resides above the lip 55. The biasing member 15 may aid in biasing the insert 16 and screw 20 towards the bottom surface 51 of the housing 30. The retainer assembly 13 may maintain the screw 20 in the housing 30 in the absence of a rod. Once the screw 20 and retainer assembly 13 are disposed within the housing 30, the retaining ring 114 may prevent the screw 20 from being removed through the bottom of the bore 44 and the biasing member 15 and insert 16 may prevent the screw 20 from being removed through the top of the bore.

Figure 9:
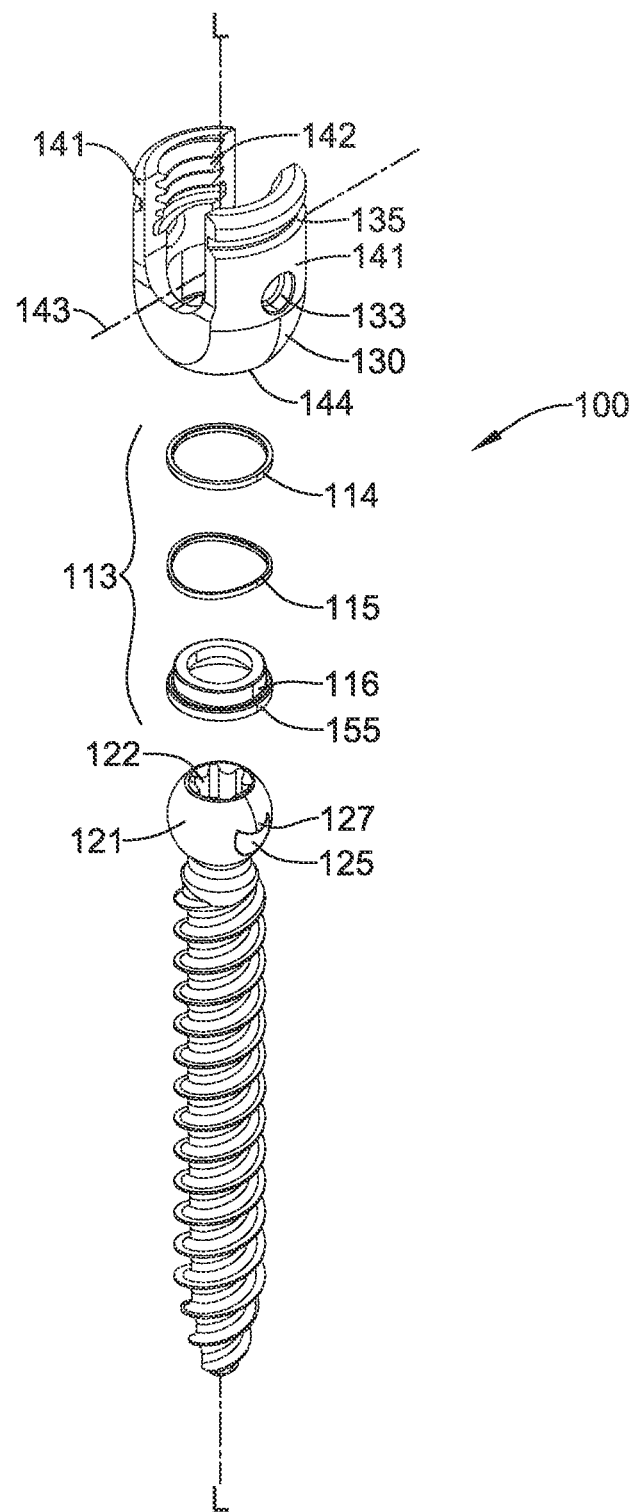
FIG. 9 is a perspective exploded view of components of another exemplary bone anchor.

Another example of uniplanar bone anchor 100 is shown in FIGS. 9-17. FIG. 9 is an exploded view illustrating components of bone anchor 100. The bone anchor 100 may include a housing 130, a bone screw 120, and a retainer assembly 113. Bone anchor 100 may be referred to as a top loading system, with the bone screw 120 inserted through the top of the housing 130. Similar to the bone anchor 10 described above, the bone anchor 100 may be screwed into a vertebra and may serve to couple a rod or other elongate member (not shown) extending along a portion of a spinal column. The rod or elongate member may fit into a U-shaped channel 143 formed by opposing arms 141 of the housing 130. The bone anchor 100 may include particular degrees of adjustability within a single plane, ensuring that, when multiple bone anchors are used with a single rod, each screw may be locked down at the particular locations and orientations desired by the practitioner, and the housings may be adjusted to a desired position within the single plane to receive the rod.

Figure 10:
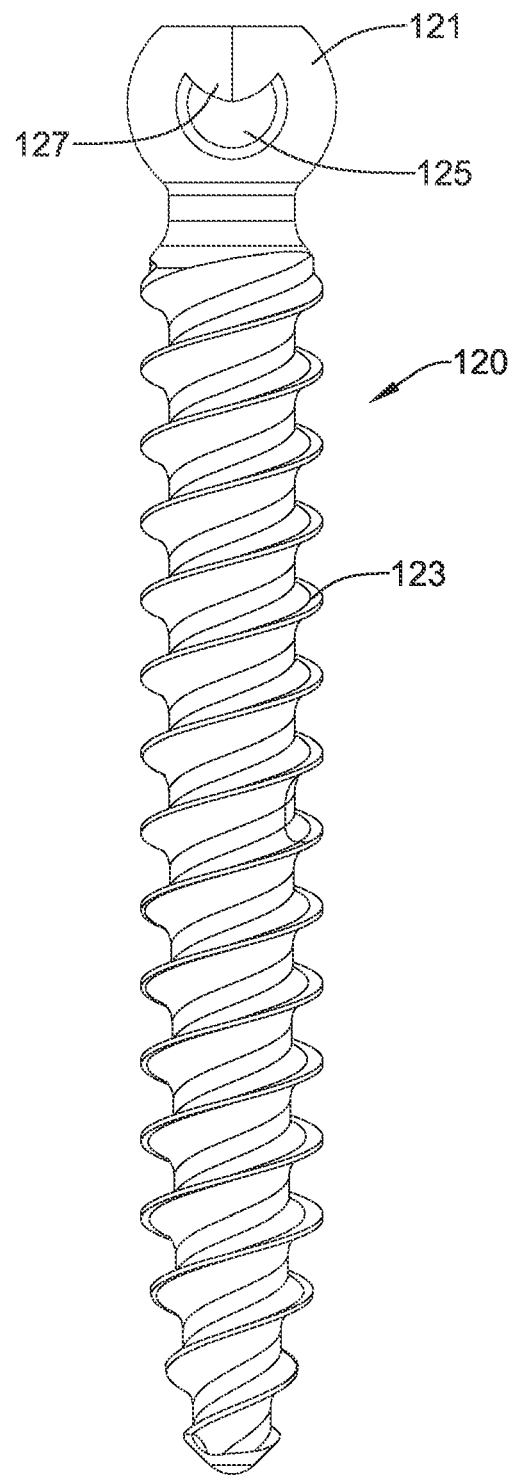
FIG. 10 is a side view of the bone screw of FIG. 9.
Figure 11:
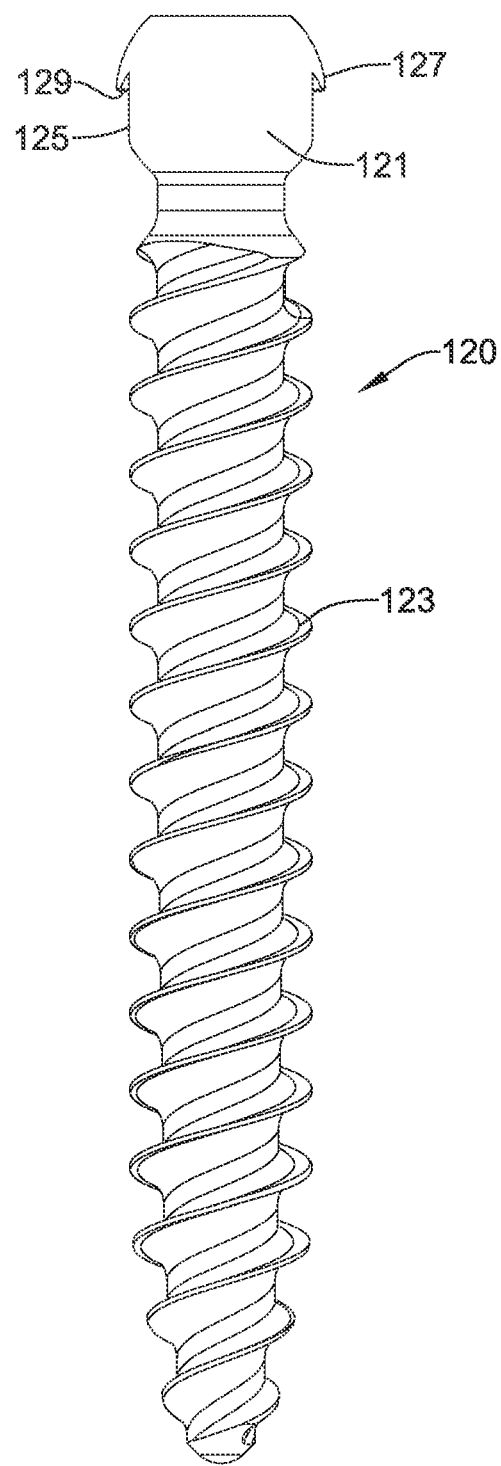
FIG. 11 is a side view of the bone screw of FIG. 9 transverse to the view of FIG. 10.

As shown in FIGS. 9-11, the screw 120 may have a threaded shank 123 configured to extend out the bottom opening of the housing 130 and engage a vertebra. The screw 120 may be a monolithic, single piece structure. The screw 120 may have a head 121 that is generally spherical in shape with opposing planar surfaces 125 and extensions 127. The extensions 127 may follow the spherical surface of the head 121, with planar surfaces 125 formed by removal of material under the extensions 127. An undercut 129 may be formed under the extensions 127 such that extensions 127 define an overhang or lip. The extensions 127 and planar surfaces 125 may be on opposite sides of the screw head 121, as shown in FIGS. 10 and 11.

Figure 12:
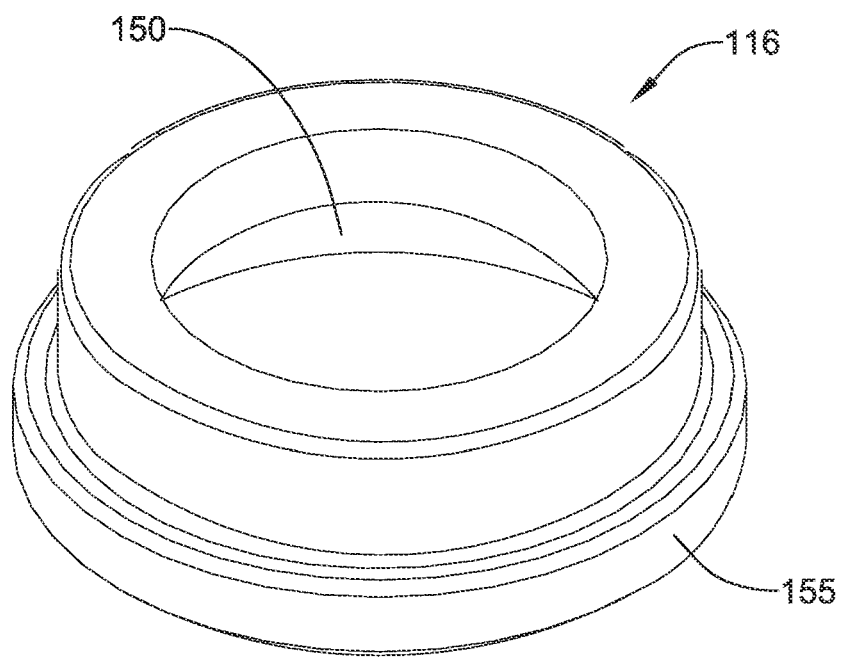
FIG. 12 is a perspective view of the insert of the apparatus of FIG. 9.
Figure 16:
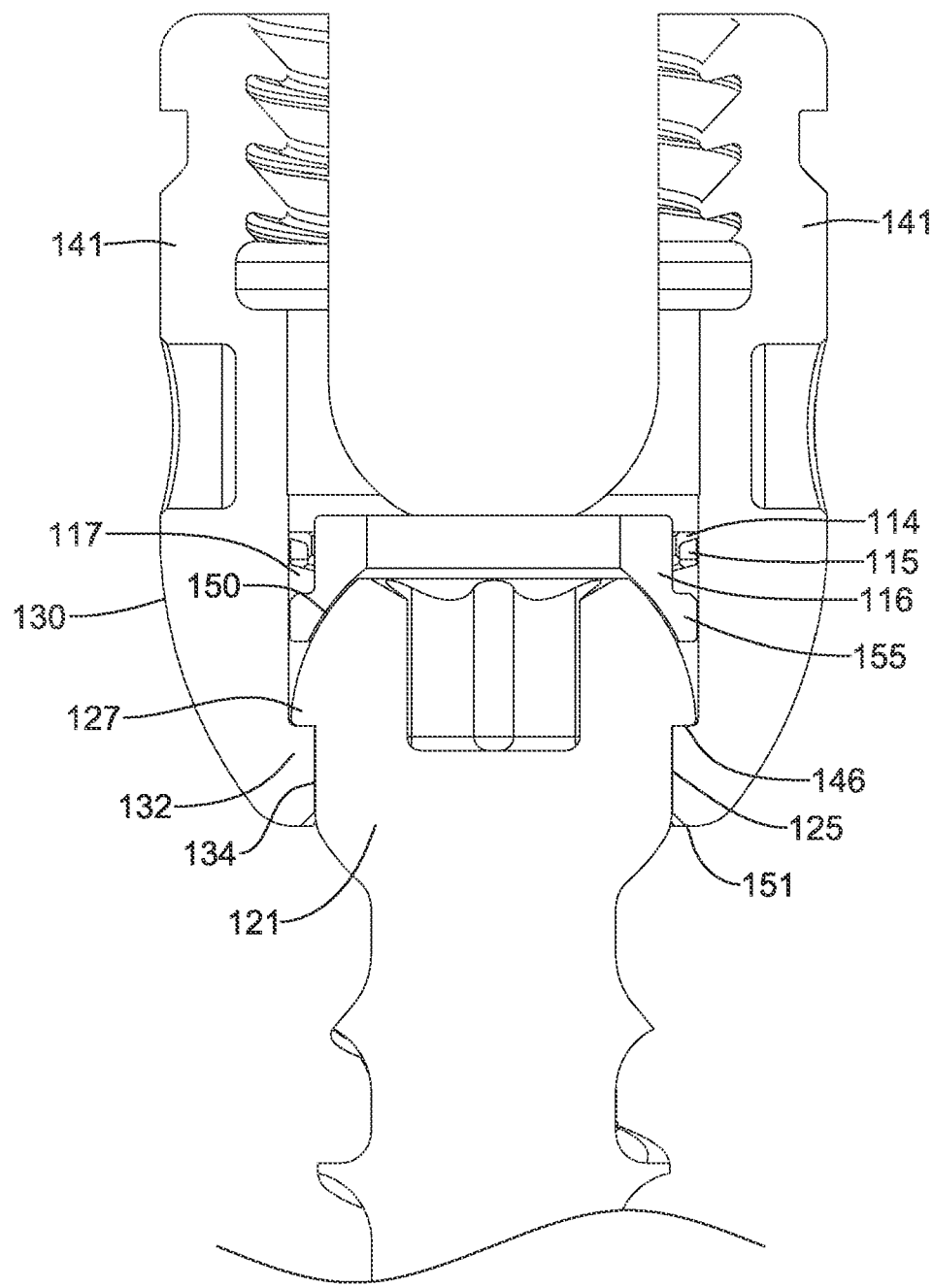
FIG. 16 is a cross-sectional view of the assembled bone anchor of FIG. 9.

The retainer assembly 113 may be in the form of one or more rings having a central aperture, which may allow the practitioner to insert a screwdriver through the aperture of the rings to engage a driver interface such as a keyed portion 122 on the head 121 of the screw 120. The exemplary retainer assembly 113 shown in FIGS. 9 and 15 includes an insert 116 that may contact the head 121 of the screw 120, a biasing member 115, and a retaining ring 114. The retaining ring 14 may be a continuous ring, as shown in FIG. 9, or it may be a split ring. The biasing member 115 may be a wave washer as shown in FIG. 9. As seen in FIGS. 12 and 16, the insert 116 may include a concave inner annular surface 150 that has a radius of curvature matched to that of the screw head 121, so that when the screw 120 is pivoted within the housing 130, it may remain held in place by the insert 116. The insert 116 may have an annular lower lip 155. The structure of the housing 130 and retainer assembly 113 in combination with the planar surfaces 125 and extensions 127 on the screw head 121 may allow pivoting of the screw head 121 in a single plane with respect to the housing 130.

Figure 13:
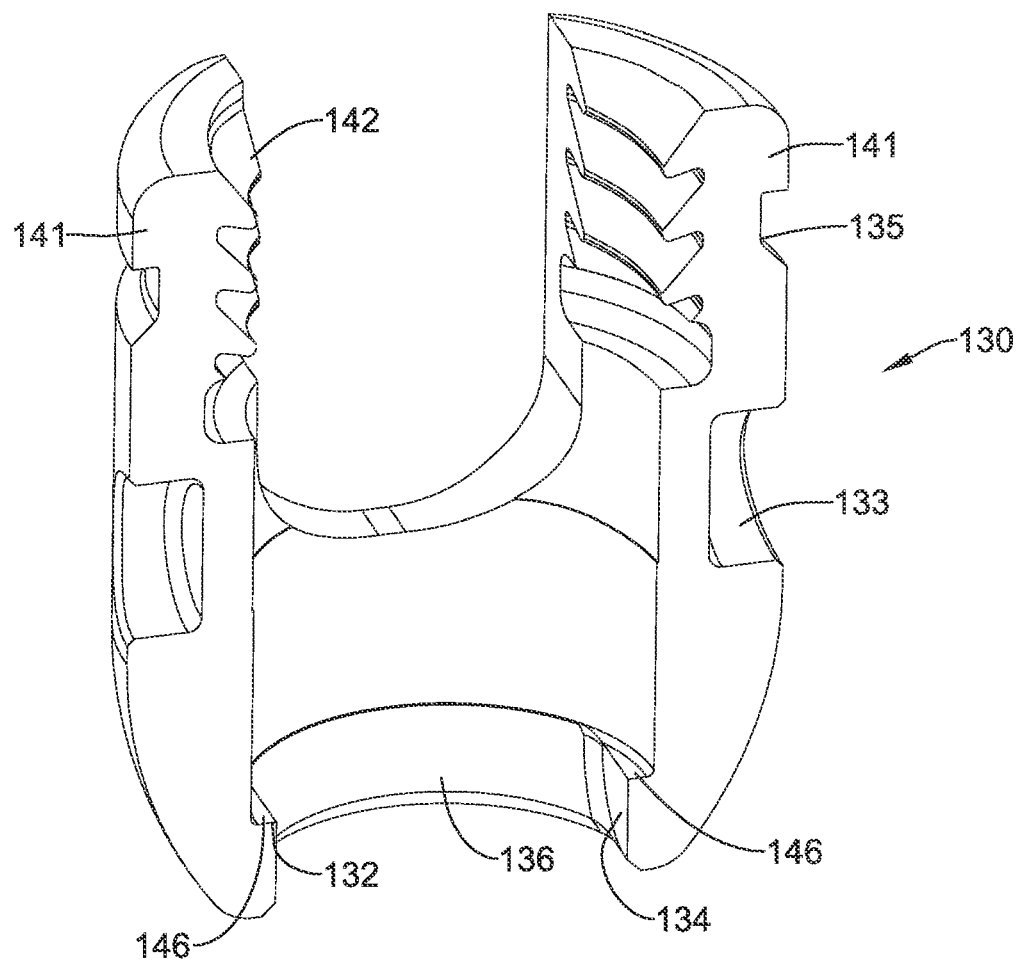
FIG. 13 is a cross-sectional partially elevated view of the housing of the anchor of FIG. 9.

As seen in FIG. 13, the housing 130 may be monolithic, thus formed as a single piece. In other examples the housing 130 may be formed of multiple pieces that are connected prior to use. The housing 130 may have a bore 144 extending through the housing 130 along the longitudinal axis L-L of the housing, transverse to the U-shaped channel 143. The screw 120 may be received in the bore 144 through the top of the housing 130. Threading 142 may be provided on the inner surface of the arms 141 for connection with a fastener or set screw (not shown). The housing 130 may include additional features such as recesses 133 or grooves 135 for interaction with insertion tools, extension sleeves, reduction tools, etc.

Figure 14:
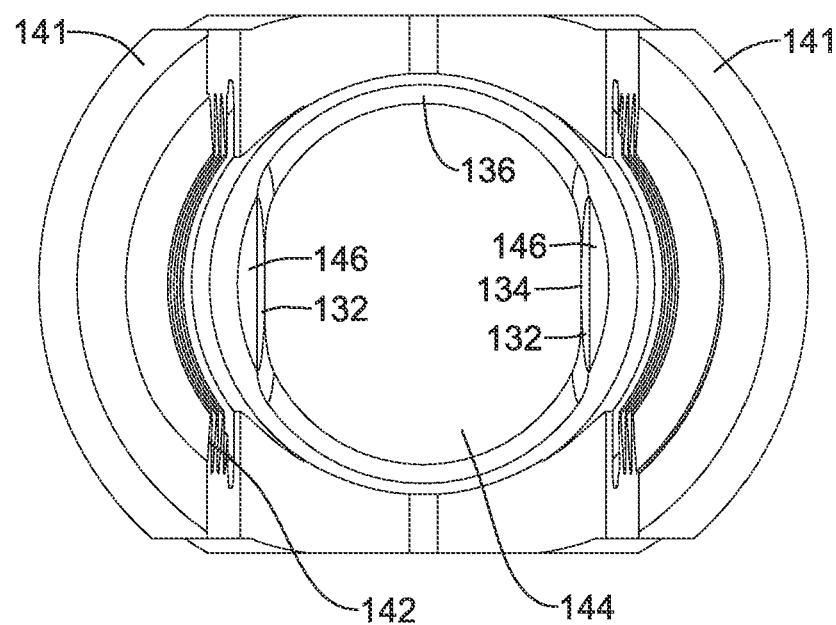
FIG. 14 is a top view of the housing of FIG. 9.
Figure 15:
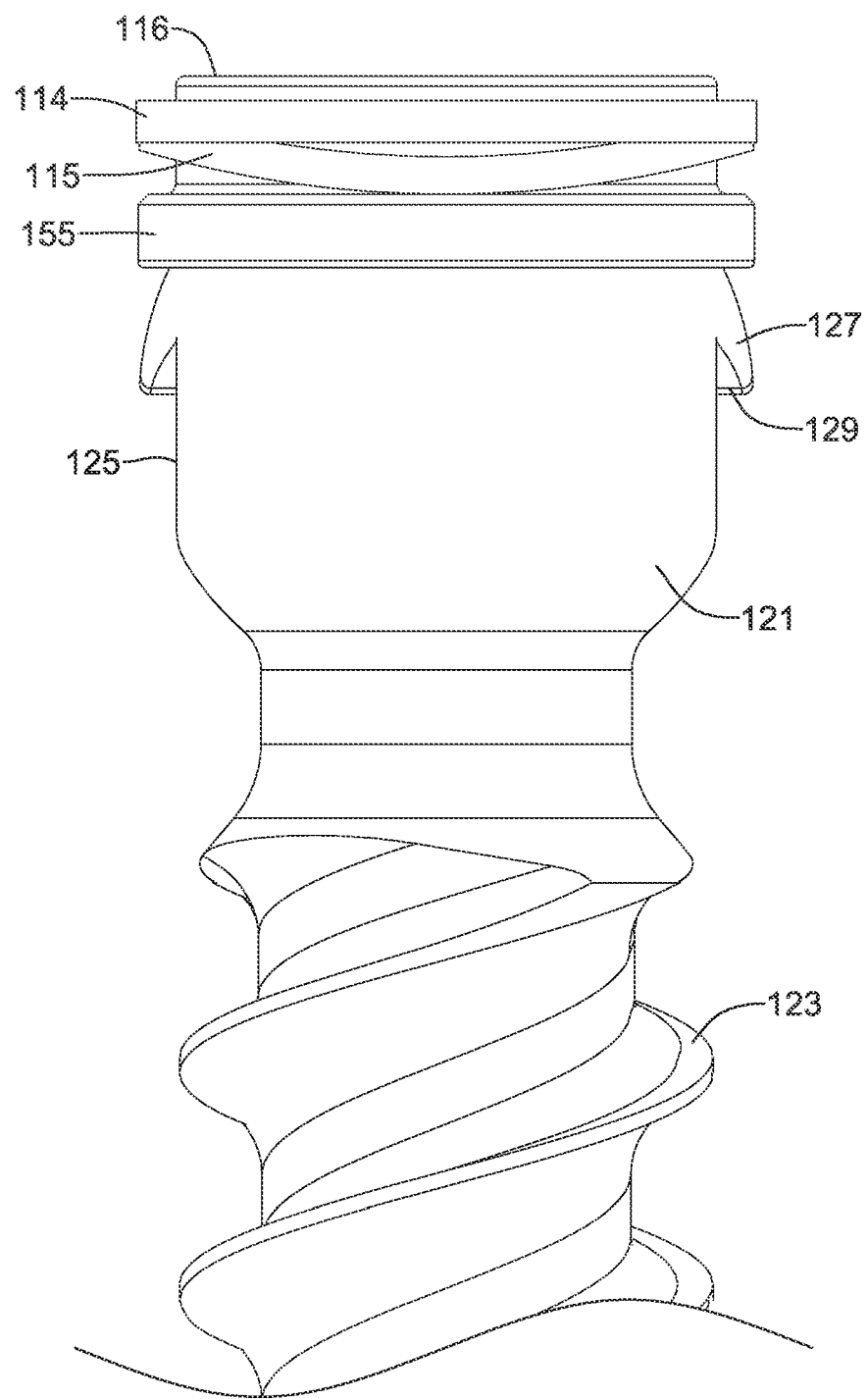
FIG. 15 is a side view of the assembled bone anchor of FIG. 9, without the housing.

The housing 130 may include opposing mating elements 132 extending from an inner wall of the housing 130 into the bore 144, transverse to the longitudinal axis L-L of the housing. The mating elements 132 may include discrete portions extending from an inner wall of the housing 130 into the bore 144 as seen in FIGS. 13 and 14. The mating elements 132 may have opposing planar surfaces 134 extending along the longitudinal axis L-L. The mating elements 132 may define upper surfaces 146. The remaining inner surface of the inner wall at the bottom of the housing may define opposing curved surfaces 136. The curved surfaces 136 may be configured to mate with the spherical surface of the screw head 121, and the planar surfaces 134 may be configured to mate with the planar surfaces 125 of the screw head 121. The extensions 127 and associated undercuts 129 on the screw head 121 may be configured to mate with the upper surfaces 146 of the mating elements 132. The mating of the planar surfaces 134 of the housing with the planar surfaces 125 of the screw head 121 may prevent rotation of the screw 120 around the longitudinal axis L-L. The mating of the curved surfaces 136 of the housing with the spherical surface of the screw head 121 may allow movement of the screw head 121 within a single plane. As shown in phantom in FIG. 17, the screw 120 may be moved within a single plane to various positions relative to the housing 130.

Figure 17:
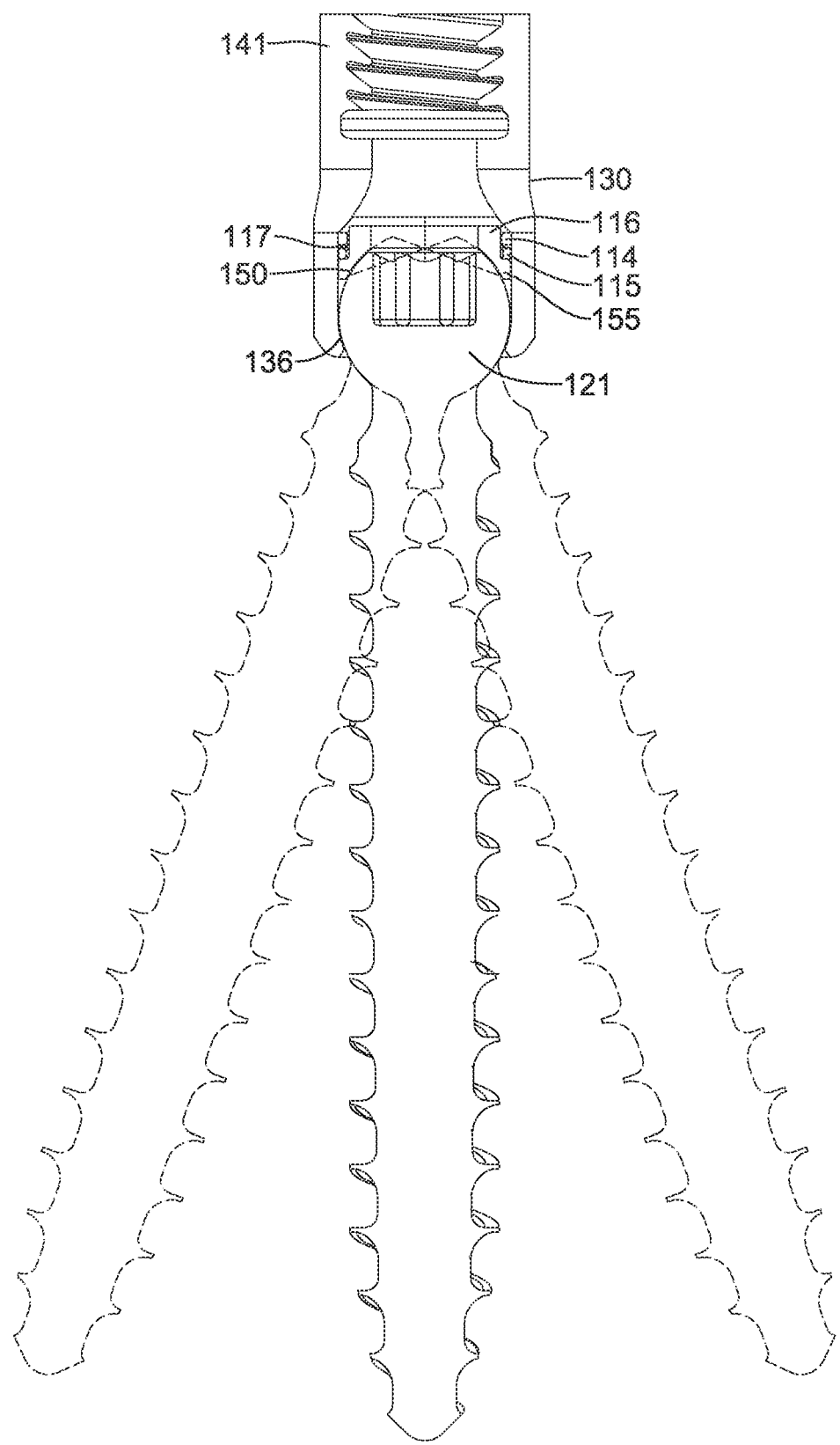
FIG. 17 is a cross-sectional view of the assembled bone anchor of FIG. 9 transverse to the cross-sectional view of FIG. 16.

The bone screw 120 may be inserted through the top of the housing 130 with the threaded shank 123 extending out the bottom 151 of the housing 130, as seen in FIGS. 16 and 17. The head 121 of the screw 120 may be held in place by the retainer assembly 113. The mating of the extensions 127 on the screw head 121 with the upper surfaces 146 of the housing may prevent the screw 120 from being removed through the bottom of the housing 130. As seen in FIGS. 16 and 17, the retaining ring 114 and biasing member 115 are received in an annular space 117 defined between an inner wall of the housing 130 and the insert 116, above a lower lip 155 on the insert 116.

To lock the elements in place, the practitioner may screw a fastener or set screw (not shown) into threading 42, 142 at the upper portion of the housing 30, 130, which may force the rod or elongate member against the upper surface of insert 16, 116, and in turn may force the insert 16, 116 against the head 21, 121 of the screw 20, 120. Prior to final tightening of the set screw, the biasing member 15, 115 may cause the insert 16, 116 to frictionally engage the head 21, 121 of the screw 20, 120 to resist movement of the housing 30, 130 with respect to the screw 20, 120. After tightening of the set screw, the frictional force between the insert 16, 116 of the retainer assembly 13, 113 and the head 21, 121 of the screw 20, 120 may be sufficient to lock the screw 20, 120 in place with respect to the housing 30, 130. In some examples, the U-shaped channel 43, 143 may be deep enough so that the set screw does not force the rod against the bottom of the U-shaped channel 43, 143. Alternatively, the retainer assembly 13, 113 may be omitted, and the set screw may force the rod directly against the head 21, 121 of the screw 20, 120 to secure the screw 20, 120 in place.

Figure 18:
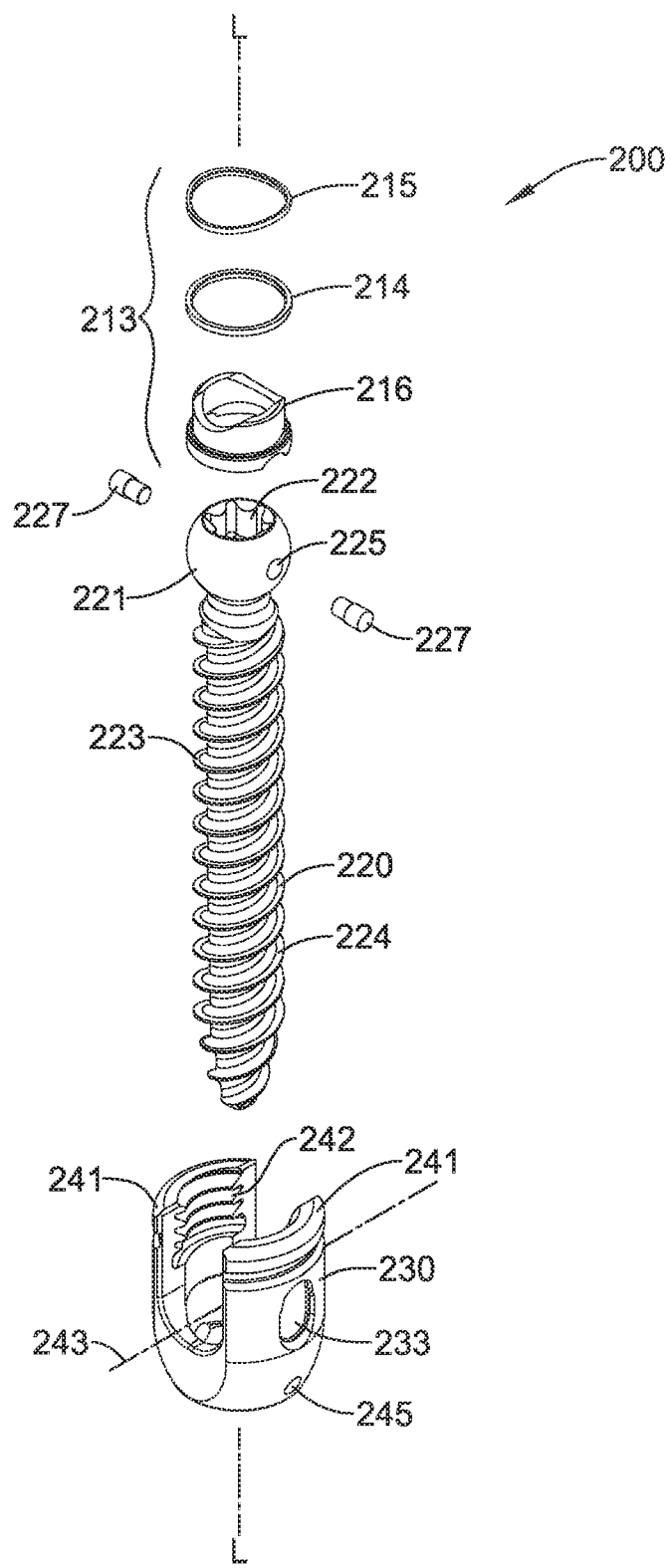
FIG. 18 is a perspective exploded view of components of another exemplary bone anchor.

Another example of top loading uniplanar bone anchor 200 is shown in FIGS. 18-23. FIG. 18 is an exploded view illustrating components of bone anchor 200. The bone anchor 200 may include a housing 230, a bone screw 220, and a retainer assembly 213. Bone anchor 200 may be referred to as a top loading system, with the bone screw 220 inserted through the top of the housing 230. Similar to the bone anchor 100 described above, the bone anchor 200 may be screwed into a vertebra and may serve to couple a rod or other elongate member (not shown) extending along a portion of a spinal column. The rod or elongate member may fit into a U-shaped channel 243 formed by opposing arms 241 of the housing 230. The bone anchor 200 may include particular degrees of adjustability within a single plane, ensuring that, when multiple bone anchors are used with a single rod, each screw may be locked down at the particular locations and orientations desired by the practitioner, and the housings may be adjusted to a desired position within the single plane to receive the rod. The structure of the housing 230 and retainer assembly 213 in combination with openings 225 in the screw head 221, openings 245 in the housing 230, and pins 227 may allow pivoting of the screw head 221 in a single plane with respect to the housing 230.

Figure 19:
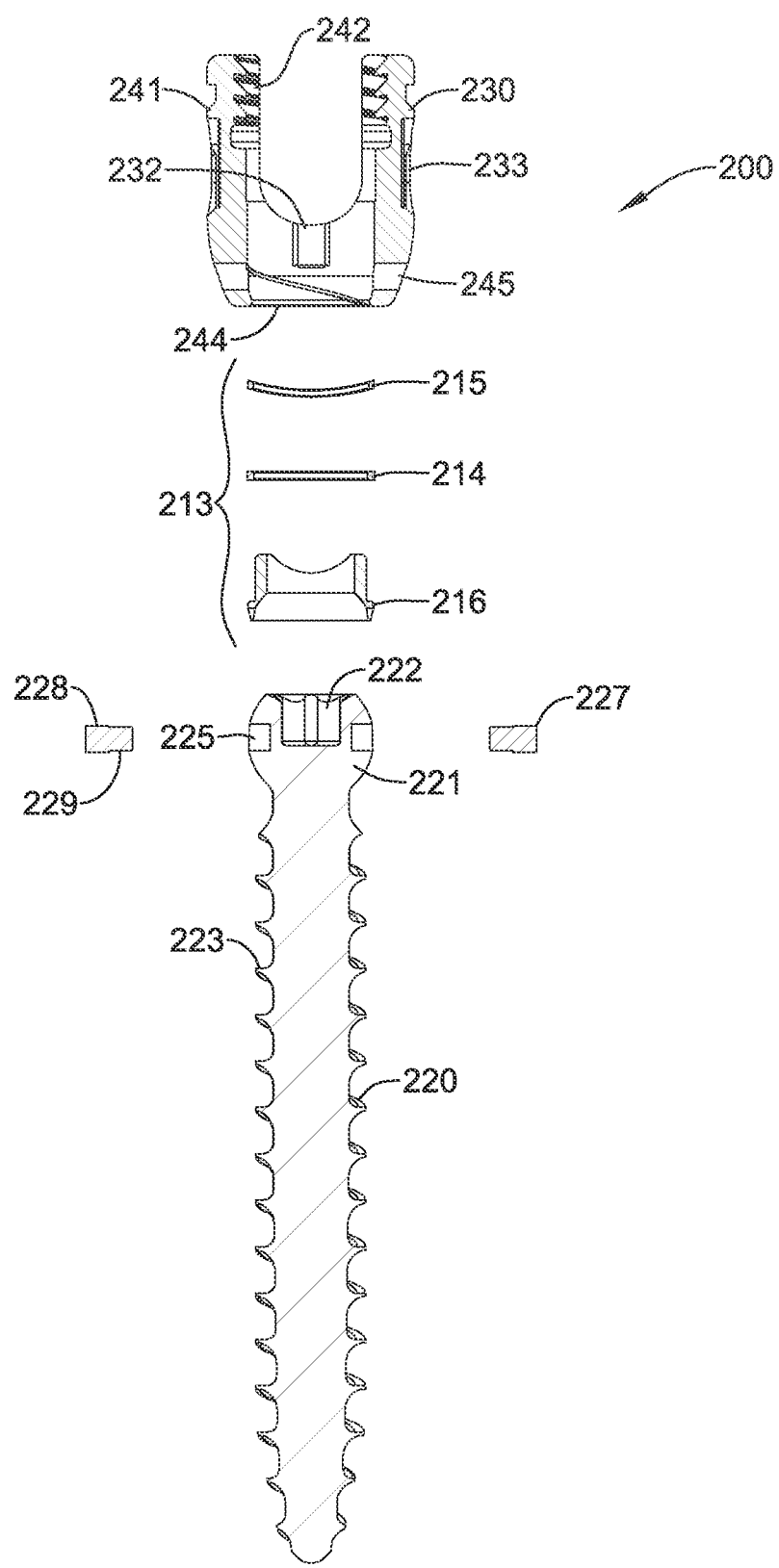
FIG. 19 is a cross-sectional exploded view of the bone anchor of FIG. 18.

As shown in FIGS. 18-19, the screw 220 may have a threaded shank 223 configured to extend out the bottom opening of the housing 230 and engage a vertebra. The screw 220 may be a monolithic, single piece structure. The screw 220 may have a head 221 that is generally spherical in shape with a pair of diametrically opposed openings 225 extending into the head 221 transverse to the longitudinal axis L of the bone anchor 200. The openings 225 are sized and configured to receive pins 227. The pins 227 may have a outer portion 228 and an inner portion 229, with the outer portion 228 having a larger diameter than the inner portion 229. See FIG. 19. The openings 245 in the housing may be sized to receive the outer portions 228 with a friction fit. The openings 225 in the screw head 221 may have a diameter greater than the diameter of the inner portion 229, allowing for a gap between the inner portion 229 and the inner wall of the opening 225, which may provide for some longitudinal movement of the screw head 221 relative to the pins 227. See FIG. 22. In another example bone anchor a single pin 227 may be used with a housing 230 having one opening 245 and a bone screw 220 having one opening 225. The single pin 227 may restrict movement of the screw 220 relative to the housing 230 to a single plane.

Figure 20:
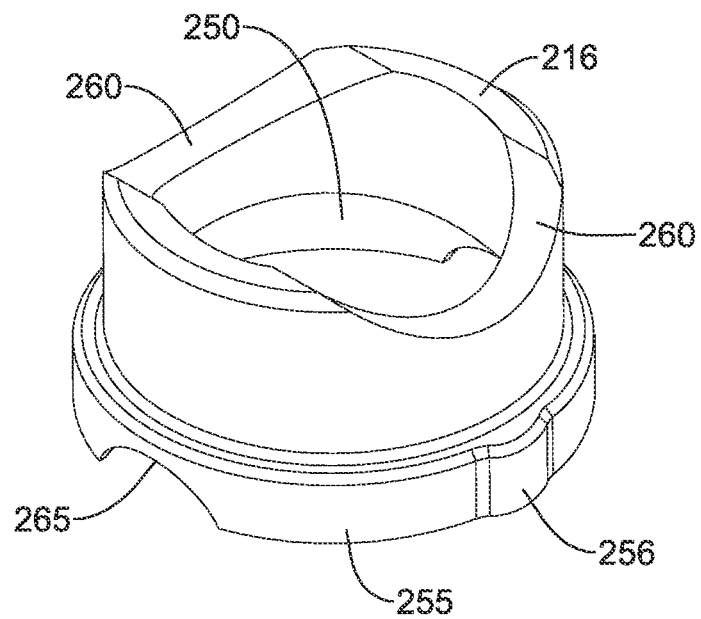
FIG. 20 is a perspective view of the insert of FIG. 18.
Figure 23:
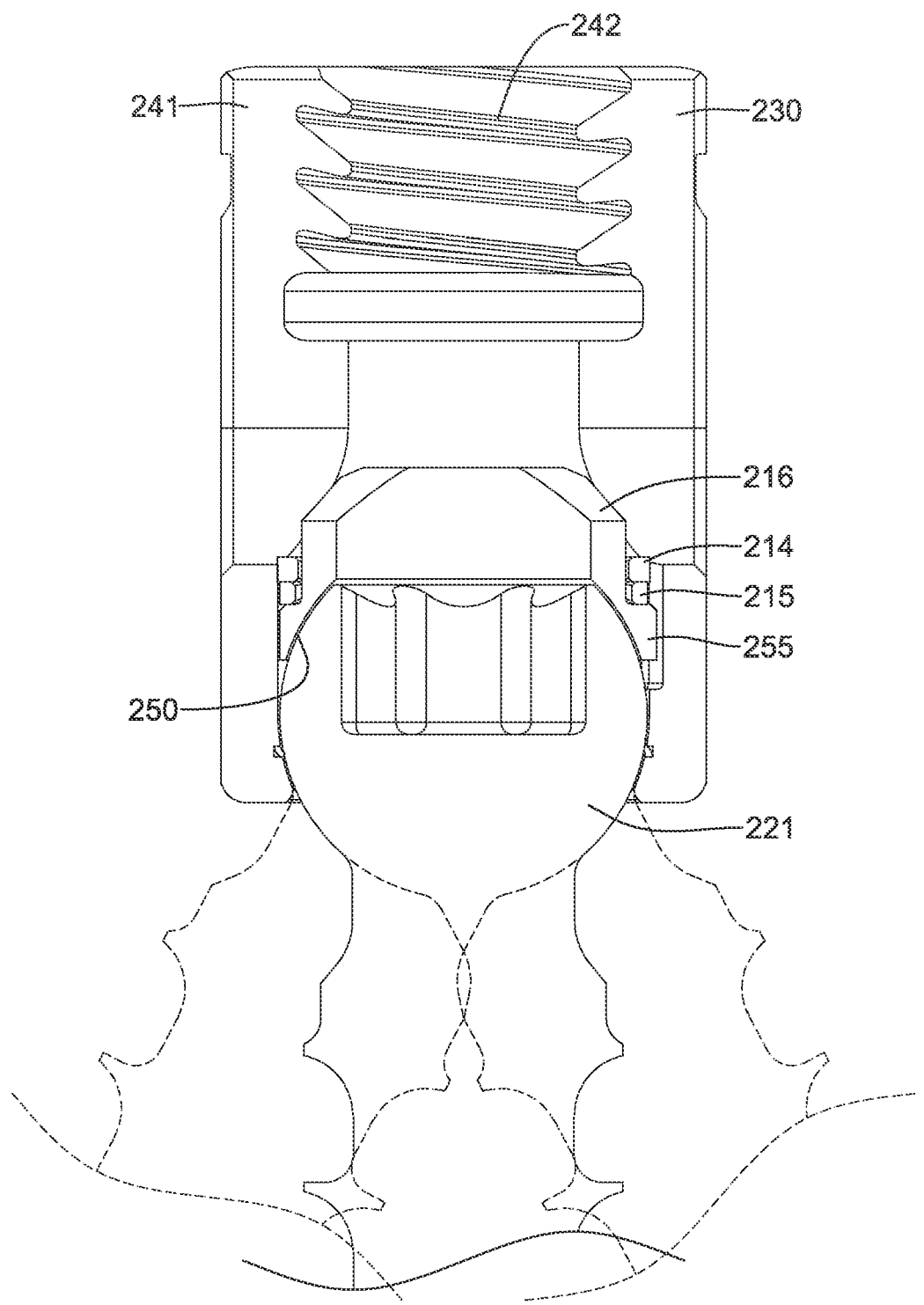
FIG. 23 is a cropped cross-sectional view of the assembled bone anchor of FIG. 18 transverse to the cross-sectional view of FIG. 22.

The retainer assembly 213 may be in the form of one or more rings having a central aperture, which may allow the practitioner to insert a screwdriver through the aperture of the rings to engage a driver interface such as a keyed portion 222 on the head 221 of the screw 220. The exemplary retainer assembly 213 shown in FIG. 18 includes an insert 216 that may contact the head 221 of the screw 220, a biasing member 215, and a retaining ring 214. The retaining ring 214 may be a continuous ring, as shown in FIG. 18, or it may be a split ring. The biasing member 215 may be a wave washer as shown in FIG. 18. As seen in FIGS. 20 and 23, the insert 216 may include a concave inner annular surface 250 that has a radius of curvature matched to that of the screw head 221, so that when the screw 220 is pivoted within the housing 230, it may remain held in place by the insert 216. The insert 216 may have a pair of diametrically opposed concave part cylindrical surfaces 260. The surfaces 260 may engage the rod when the surfaces 260 are aligned with a channel 243 in the housing 230 through which the rod extends. The insert 216 may have a pair of diametrically opposed cut-outs 265 which may allow the insert 216 to be positioned over the screw head 221 without interfering with the insertion of the pins 227 into the openings 225 on the screw head 221. The insert 216 may have an annular lower lip 255. The annular lower lip 255 may have a key feature such as an extension 256, which mates with a corresponding key feature such as a recess 232 in the housing 230. See FIG. 21.

As seen in FIG. 18, the housing 230 may be monolithic, thus formed as a single piece. In other examples the housing 230 may be formed of multiple pieces that are connected prior to use. The housing 230 may have a bore 244 extending through the housing 230 along the longitudinal axis L-L of the housing, transverse to the U-shaped channel 243. The screw 220 may be received in the bore 244 through the top of the housing 230. At least an upper portion of arms 241 may include threading 242 on an inner surface thereof. Threading 242 may have a form, pitch, and size to conform to the threads on a fastener such as a set screw (not shown). The inner surface of at least the lower portion of the housing 230 may include threading 240 having a form, pitch, and size configured to allow the threaded screw shank 223 to pass through. See FIGS. 19 and 21. The threading 240 inside the lower portion of the housing 230 may allow for a wide variety of screw diameters to be used. When a diameter of the screw shaft is smaller than the inner diameter of the lower portion of the housing, the screw may be dropped through the bore 244 with only the screw head 221 engaging the housing 230. The threading 240, however, allows for a larger diameter screw to be inserted. As a larger diameter screw is inserted into the interior cavity of housing 230, the threading 224 on the screw 220 include substantially the pitch to engage threading 240 which extend through to the lower end of housing 230. In this manner, a polyaxial screw 220 can be screwed into position until the screw head 221 rests on the curved surface 236 at the lower portion of the housing 230. In some examples, threading 240 may extend from the lower end of threading 242.

This construction may allow a bone screw 220 having a larger shaft 223 diameter than the bore 244 of the housing 230 to be inserted therethrough, whereby the screw head 221 will still engage the seat 237 of the housing. The thread form and pitch of the bone screw 220 do not have to match the exact thread form and pitch of the housing 230 for operation. The pitch and form of the threading 224 on the bone screw need only be constructed and arranged to threadably pass through the bore 244 without significant interference between the two components. When a smaller diameter bone screw is used, there may be sufficient clearance between the outer diameter of the threading 224 and walls of the bore 244 to easily allow the screw to be inserted through the bore until the screw head 221 rests on the seat 237 of the housing 230. So long as the screw head 221 remains the same size, this feature may also allow the interchangeability of screws of varying shaft 223 diameter while utilizing the same housing 230, retainer assembly 213, and fasteners or set screws (not shown). A kit may be provided which includes a housing 230, retainer assembly 213, and set screw (not shown), with a plurality of bone screws 220 having different outer shaft diameters allowing a surgeon to choose a bone screw for the specific patient condition.

The housing 230 may include additional features such as recesses 233 and/or grooves 235 for interaction with insertion tools, extension sleeves, reduction tools, etc.

Figure 22:
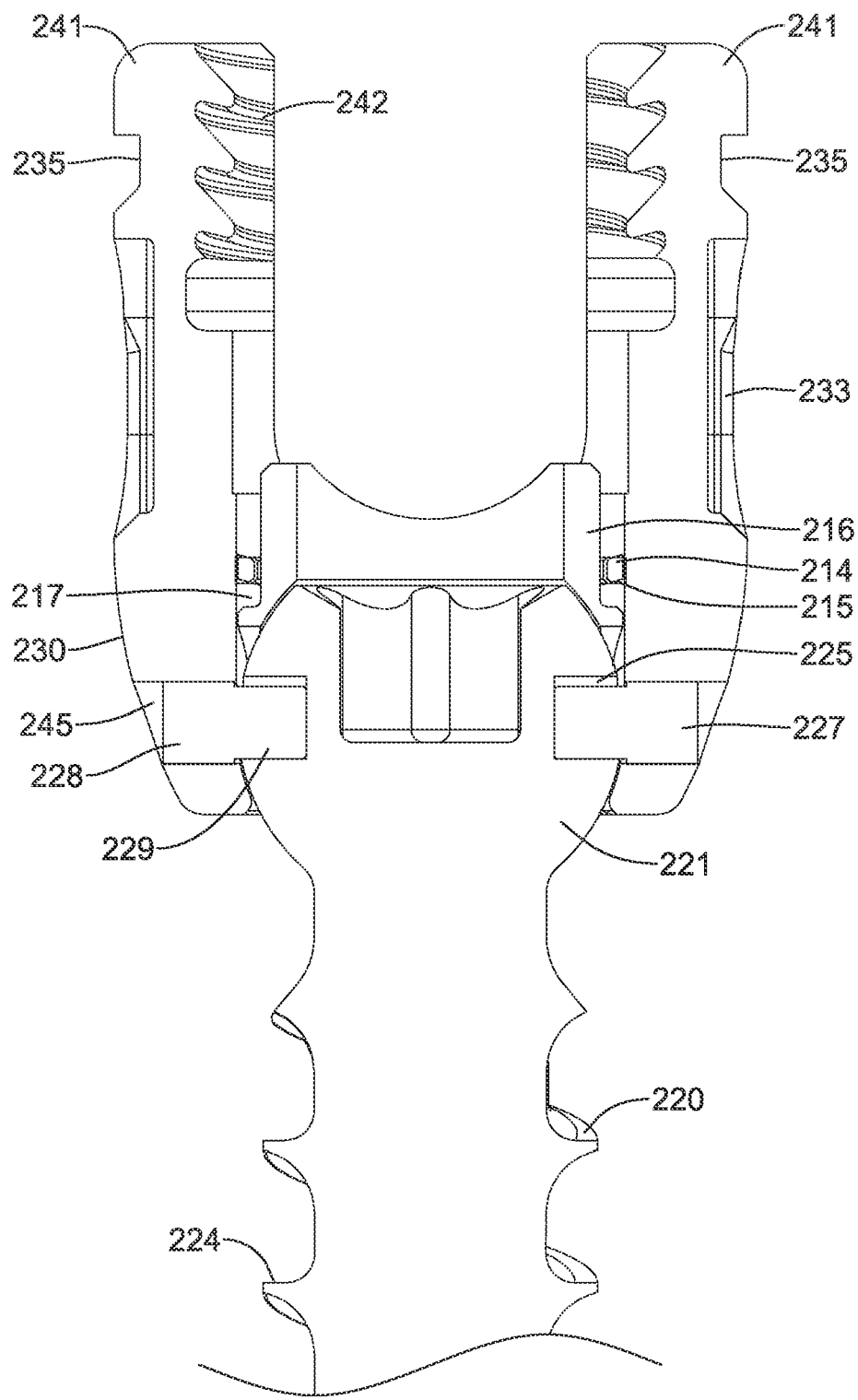
FIG. 22 is a cross-sectional view of the assembled bone anchor of FIG. 18.

The housing 230 may include a pair of diametrically opposed openings 245 extending through the wall of the housing 230 into the bore 244, transverse to the longitudinal axis L-L of the housing. The openings 245 are positioned such that when the screw head 221 is seated in the lower portion of the housing 230, the openings 245 on the housing 230 may be aligned with the openings 225 on the screw head 221. Insertion of the pins 227 through the openings 245 and 225 allows the screw 220 to be moved or pivoted within a single plane with respect to the housing 230. See FIG. 22. The diameter of the openings 245 in the housing 230 may be configured to receive the outer portion 228 of the pins 227 with a friction fit. The pins 227 have a length such that the second portion may be seated within the opening 225 in the screw head 221 and the outer portion 228 extends into the opening 245 in the housing 230, as shown in FIG. 22. The slightly larger opening 225 compared to the inner portion 229 of the pin 227 allows the screw head 221 to move distally when the rod is inserted and tightened.

Insertion of the pins 227 through openings 245 of the housing and openings 225 of the screw head 221 may prevent rotation of the screw 220 around the longitudinal axis L-L, and in combination with the mating of the curved surface 236 of the housing with the spherical surface of the screw head 221, may allow movement of the screw head 221 within a single plane. As shown in phantom in FIG. 23, the pins 227 allow the screw 220 to be moved within a single plane to various positions relative to the housing 230.

Figure 21:
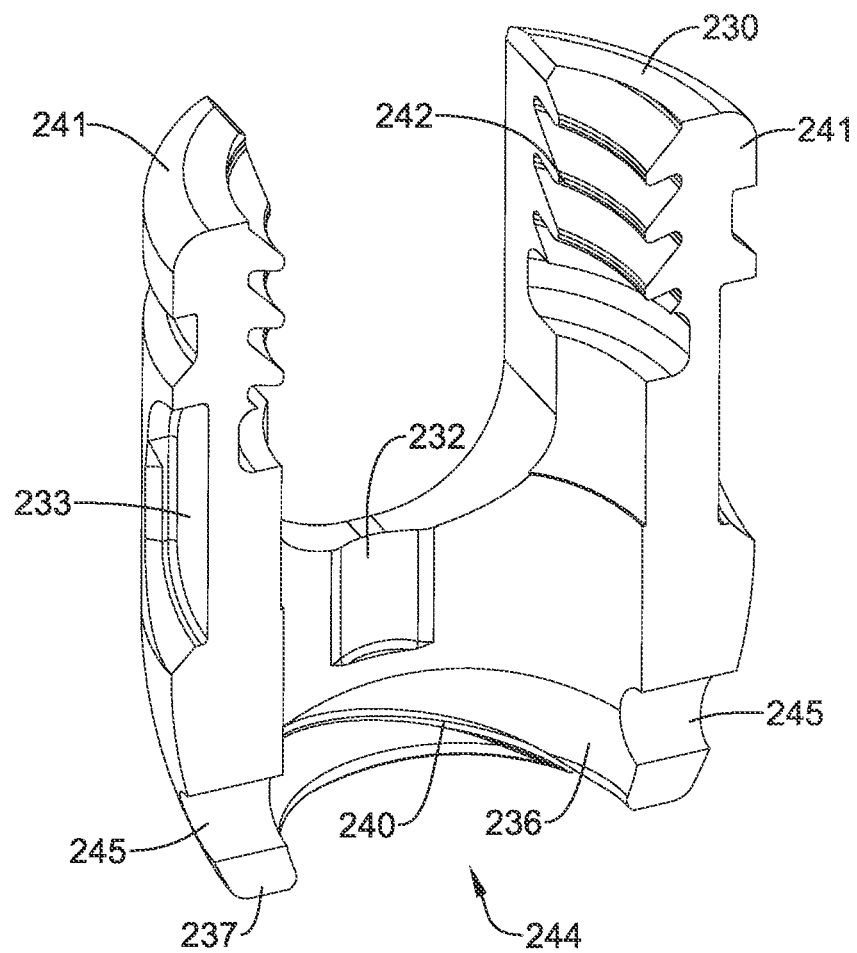
FIG. 21 is a cross-sectional partially elevated view of the housing of FIG. 18.

The bone screw 220 may be inserted through the top of the housing 230 with the threaded shank 223 extending out the bottom of the housing 230, as seen in FIGS. 21 and 23. The head 221 of the screw 220 may be held in place by the retainer assembly 213. The insertion of the pins 227 through the openings 245 in the housing 230 and into the openings 225 on the screw head 221 may prevent the screw 220 from being removed through the bottom of the housing 230. As seen in FIGS. 21 and 23, the retaining ring 214 and biasing member 215 are received in an annular space 217 defined between an inner wall of the housing 230 and the insert 216, above a lower lip 255 on the insert 216.

Figure 24:
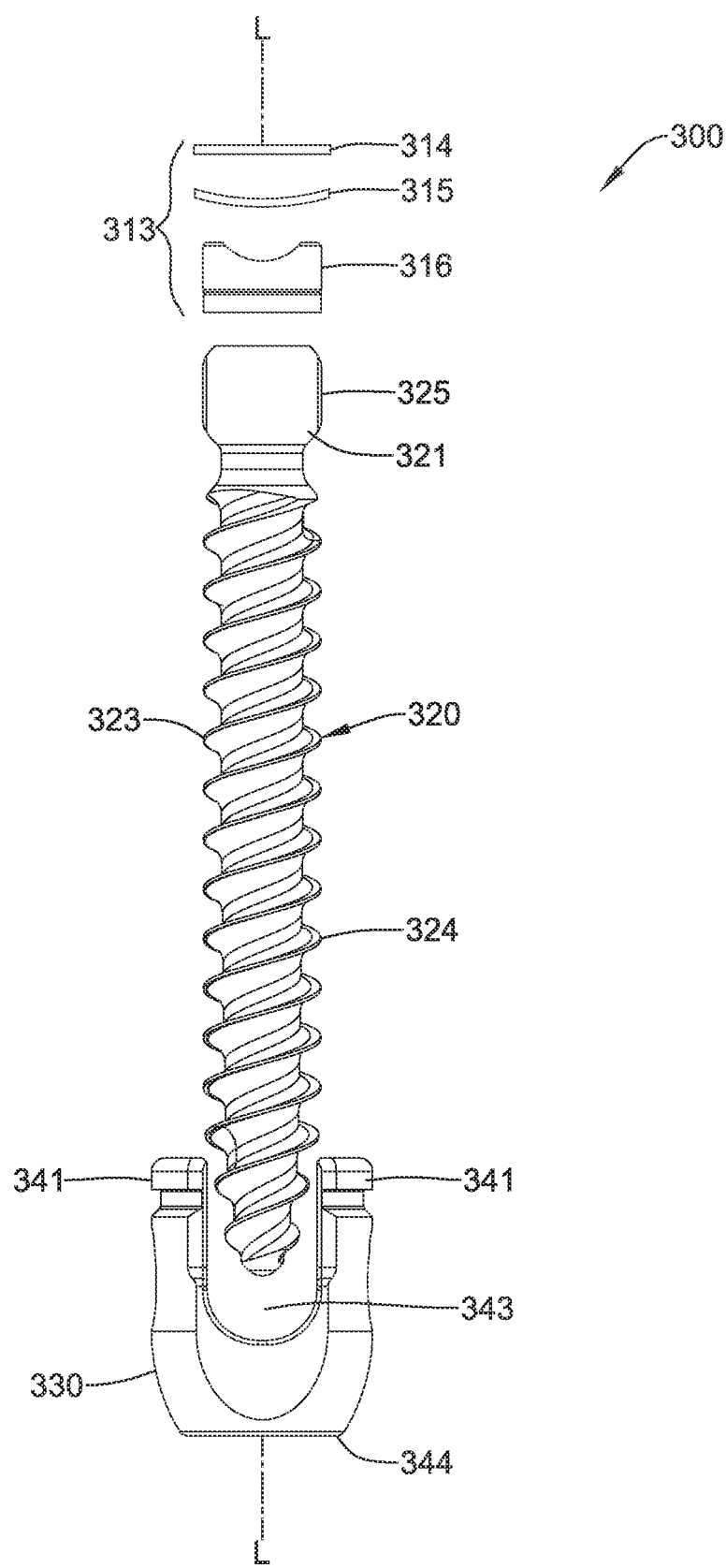
FIG. 24 is an exploded elevational view of components of another exemplary bone anchor.
Figure 25:
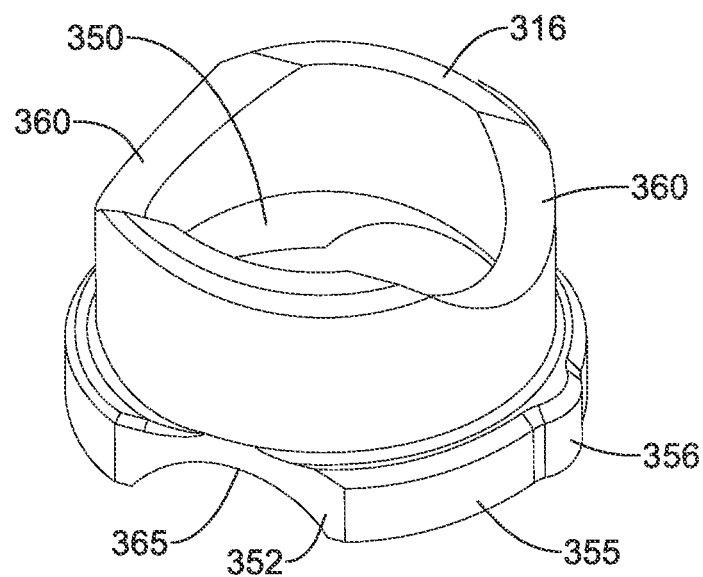
FIG. 25 is a perspective view of the insert of FIG. 24.

Another example of uniplanar bone anchor 300 is shown in FIGS. 24-28. FIG. 24 is an exploded view illustrating components of bone anchor 300. The bone anchor 300 may include a housing 330, a bone screw 320, and a retainer assembly 313. Bone anchor 300 may be referred to as a top loading system, with the bone screw 320 inserted through the top of the housing 330 as shown in FIG. 24. Similar to the bone anchors 10, 100, 200 described above, the bone anchor 300 may be screwed into a vertebra and may serve to couple a rod or other elongate member (not shown) extending along a portion of a spinal column. The rod or elongate member may fit into a U-shaped channel 343 formed by opposing arms 341 of the housing 330. The bone anchor 300 may include particular degrees of adjustability within a single plane, ensuring that, when multiple bone anchors are used with a single rod, each screw may be locked down at the particular locations and orientations desired by the practitioner, and the housings may be adjusted to a desired position within the single plane to receive the rod.

The bone screw 320 may be similar in structure and function to the bone screw 20 described above and shown in FIGS. 1-3. The screw 320 may have a threaded shank 323, a head 321 that is generally spherical in shape with opposing planar surfaces 325, and a driver interface such as a keyed portion 322. The retainer assembly 313 may have a similar structure and function as the retainer assembly 213 described above and shown in FIGS. 18-20. The retainer assembly 313 may include a retaining ring 314, a biasing member 315, and an insert 316 with a concave inner annular surface 350 that has a radius of curvature matched to that of the screw head 321. The insert 316 may have a pair of diametrically opposed concave part cylindrical surfaces 360 configured to engage the rod when the surfaces 360 are aligned with a channel 343 in the housing 330 through which the rod extends. The insert 316 may have opposing planar surfaces 352 which may include cut-outs 365 that, when aligned with the planar surfaces 325 of the screw head 321, may allow the screw head 321 and insert 316 to fit within the interior of the housing 330. The insert 316 may have an annular lower lip 355 extending laterally away from the body of the insert, and may include a key feature such as an extension 356, which mates with a corresponding key feature such as a recess 332 in the housing 330. See FIGS. 25 and 26. The biasing member 315 may be placed over the insert 316 such that the biasing member resides above the lip 355. The biasing member 315 may aid in biasing the insert 316 and screw 320 towards the bottom of the housing 330.

Figure 26:
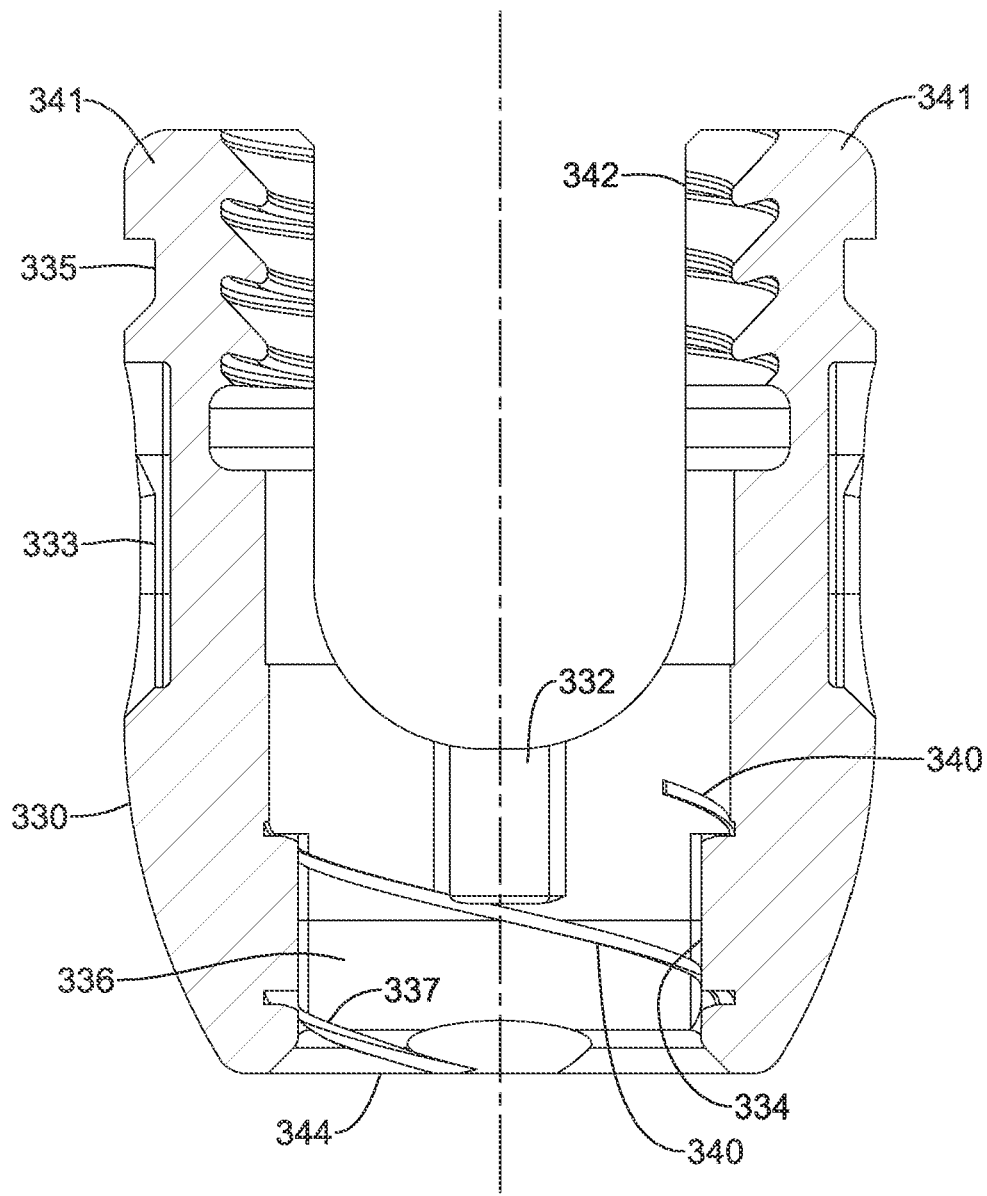
FIG. 26 is a cross-sectional view of the housing of FIG. 24.
Figure 27:
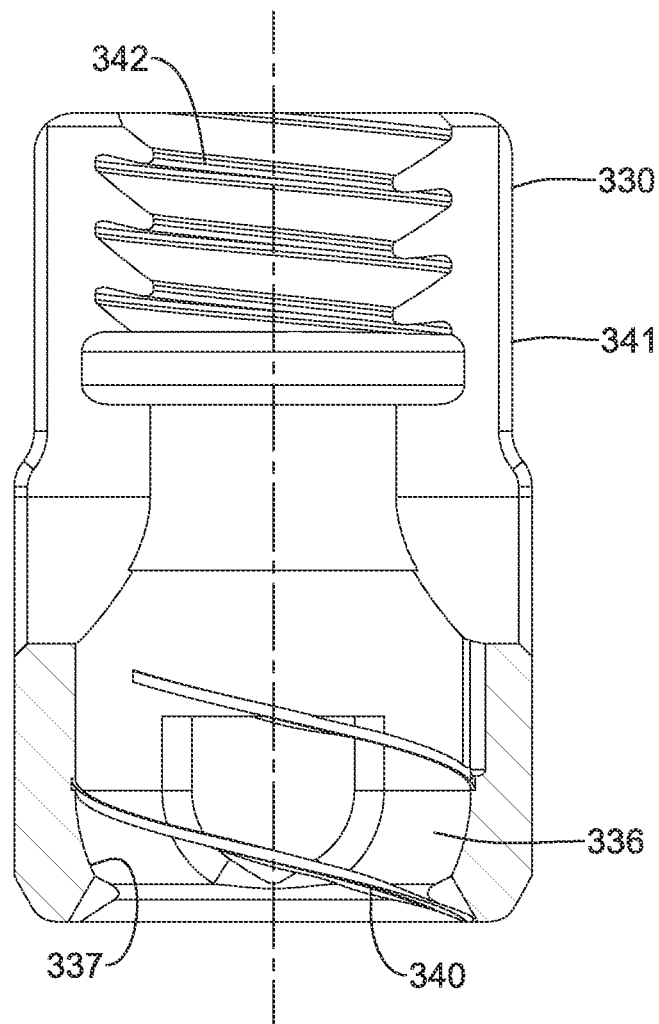
FIG. 27 is a cross-sectional view of the housing of FIG. 24 transverse to the cross-sectional view of FIG. 26.
Figure 28:
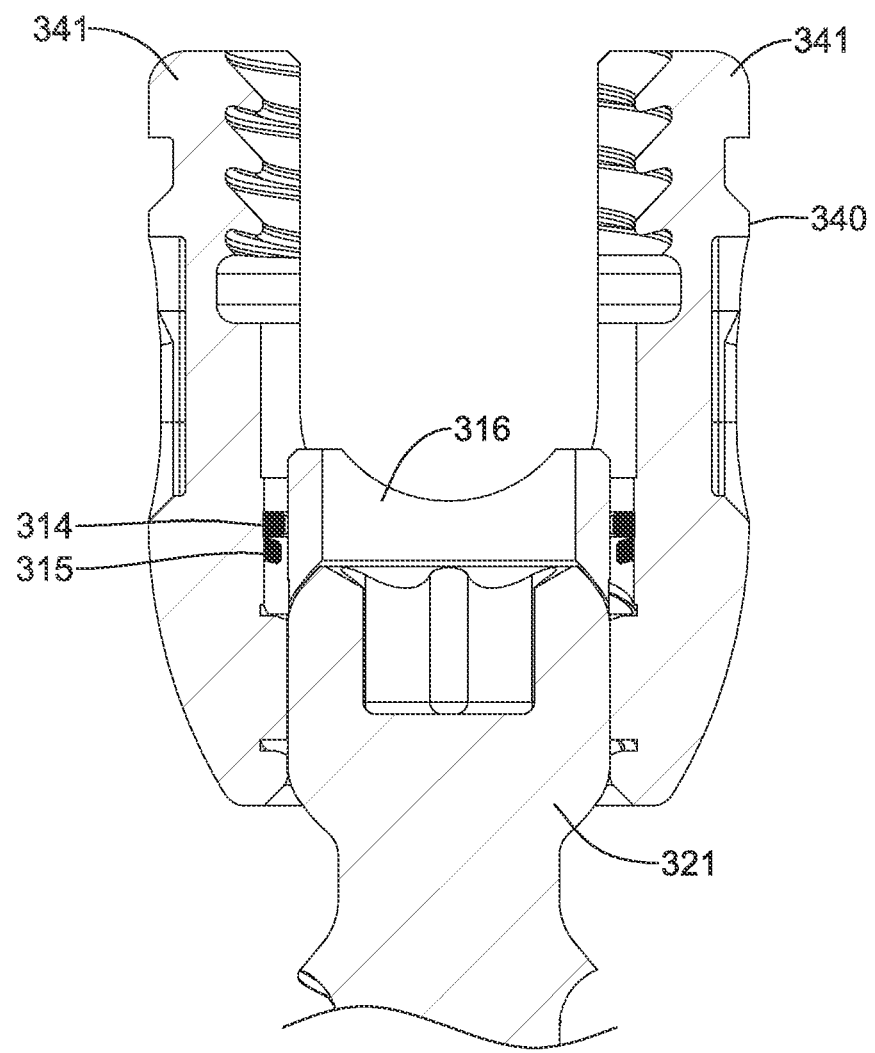
FIG. 28 is a cross-sectional view of the assembled bone anchor of FIG. 24.

As seen in FIG. 26, the housing 330 may be monolithic, thus formed as a single piece. In other examples the housing 330 may be formed of multiple pieces that are connected prior to use. The housing 330 may have a bore 344 extending through the housing 330 along the longitudinal axis L-L of the housing, transverse to the U-shaped channel 343. The screw 320 may be received in the bore 344 through the top of the housing 330. The housing may include a seat 337 extending partially into the bore 344 to prevent the screw 320 from being removed through the bottom of the housing 330. At least an upper portion of arms 341 may include threading 342 on an inner surface thereof. Threading 342 may have a form, pitch, and size to conform to the threads on a fastener such as a set screw (not shown). The inner surface of at least the lower portion of the housing 330 may include threading 340 having a form, pitch, and size configured to allow the threaded screw shank 323 to pass through. See FIGS. 26 and 27.

As discussed above with reference to the example shown in FIGS. 18-23, the threading 340 inside the lower portion of the housing 330 may allow for a wide variety of screw diameters to be used. A smaller diameter screw shaft may be dropped through the bore 344 with only the screw head 321 engaging the housing 330, while a larger diameter screw with threads 324 having substantially the pitch to engage threading 340 allows a polyaxial screw 320 to be screwed into position until the screw head 321 rests on the seat 337 at the lower portion of the housing 330. In some examples, threading 340 may extend from the lower end of threading 342. The thread form and pitch of the bone screw 320 do not have to match the exact thread form and pitch of the housing 330 for operation. The pitch and form of the thread 324 on the bone screw need only be constructed and arranged to threadably pass through the bore 344 without significant interference between the two components. So long as the screw head 321 remains the same size, this feature may also allow the interchangeability of screws of varying shaft 323 diameter while utilizing the same housing 330, retainer assembly 313, and fasteners or set screws (not shown). A kit may be provided which includes a housing 330, retainer assembly 313, and set screw (not shown), with a plurality of bone screws 320 having different outer shaft diameters allowing a surgeon to choose a bone screw for the specific patient condition.

The housing 330 may include additional features such as recesses 333 or grooves 335 for interaction with insertion tools, extension sleeves, reduction tools, etc. The inner surface of the housing 330 at the lower end thereof may include opposing planar surfaces 334 and opposing curved surfaces 336. The planar surfaces 334 may extend further into the bore 344 than the remainder of the inner surface of the housing 330. The curved surfaces 336 may be configured to mate with the spherical surface of the screw head 321, and the planar surfaces 334 may be configured to mate with the planar surfaces 325 of the screw head 321. The screw head 321 may be received within the housing 330 in a first orientation or a second orientation, turned 180 degrees from the first orientation. The mating of the planar surfaces 334 of the housing with the planar surfaces 325 of the screw head 321 may prevent rotation of the screw 320 around the longitudinal axis L-L. See FIG. 28. The mating of the curved surfaces 336 of the housing with the spherical surface of the screw head 321 may allow movement of the screw head 321 relative to the housing 330 with a longitudinal axis of the screw 320 being positionable in any one of a plurality of angular positions within a single plane relative to the longitudinal axis of the housing bore 344. The threading 340 on the inner surface of the housing 330 may cross the planar surfaces 334 and the curved surfaces 336. In some examples, the threading 340 may cross only the planar surfaces 334.

The bone screw 320 may be inserted through the top of the housing 330 with the threaded shank 323 extending out the bottom of the housing 330, as seen in FIGS. 24 and 26. The head 321 of the screw 320 may be held in place by the retainer assembly 313. As seen in FIG. 26, the retaining ring 314 and biasing member 315 are received in an annular space 317 defined between an inner wall of the housing 330 and the insert 316, above a lower lip 355 on the insert 316. The structure of the housing 330 and retainer assembly 313 in combination with the planar surfaces 325 on the screw head 321 may allow pivoting of the screw head 321 in a single plane with respect to the housing 330.

For simplicity purposes, the following discussion makes reference to the bone anchor 10, however this is not intended to limit the devices described herein, as the discussion may be applied to the other bone anchors 100, 200, 300.

To lock the elements in place, the practitioner may screw a fastener or set screw (not shown) into threading 42 at the upper portion of the housing 30 which may force the rod or elongate member against the upper surface of insert 16 and in turn may force the insert 16 against the head 21 of the screw 20. Prior to final tightening of the set screw, the biasing member 15 may cause the insert 16 to frictionally engage the head 21 of the screw 20 to resist movement of the housing 30 with respect to the screw 20. After tightening of the set screw, the frictional force between the insert 16 of the retainer assembly 13 and the head 21 of the screw 20 may be sufficient to lock the screw 20 in place with respect to the housing 30. In some examples, the U-shaped channel 43 may be deep enough so that the set screw does not force the rod against the bottom of the U-shaped channel 43. Alternatively, the retainer assembly 13 may be omitted, and the set screw may force the rod directly against the head 21 of the screw 20 to secure the screw 20 in place.

It is to be understood that even though numerous characteristics of various examples have been set forth in the foregoing description, together with details of the structure and function of various examples, this detailed description is illustrative only, and changes may be made in detail, especially in matters of structure and arrangements of parts illustrated by the various examples to the full extent indicated by the broad general meaning of the terms in which the appended claims are expressed. This may include, to the extent that it is appropriate, the use of any of the features of one example being used in other examples. The invention's scope is, of course, defined in the language in which the appended claims are expressed.

What is claimed is:

1. A bone anchor comprising:
  a housing including a bore with a longitudinal axis, the bore extending through the housing to a lower opening and including opposing mating elements extending inward from opposing sides of the bore, the housing including a channel for receiving an elongate member, the channel extending transverse to the bore;
  a bone screw insertable into the housing and including a head and a shank extending from the head along a longitudinal axis of the bone screw, the head including a spherical body comprising opposing planar surfaces, each planar surface of the opposing planar surfaces including an extension defining an overhanging lip adapted to engage a portion of a mating element of the opposing mating elements of the housing, the spherical body permitting movement of the head relative to the housing in a first plane and engagement of the opposing planar surfaces and opposing mating elements of the housing preventing movement of the head in a second plane orthogonal to the first plane; and
  a retainer assembly adapted to retain the bone screw within the housing.

2. The bone anchor of claim 1, wherein each of the opposing mating elements includes an upper surface configured to engage one of the overhanging lips of a respective one of the extensions when the bone screw is inserted into the housing.

3. The bone anchor of claim 1, wherein each of the opposing mating elements includes a planar surface extending along the longitudinal axis of the bore and wherein the overhanging lip overhangs an undercut and faces a posterior end of the bone screw and the engaged portion of the mating element of the opposing mating elements of the housing faces an anterior end of the bone screw.

4. The bone anchor of claim 3, wherein each planar surface of the opposing planar surfaces of the head is adapted to engage one of the planar surfaces of the mating elements when the bone screw is inserted into the housing.

5. The bone anchor of claim 1, wherein the opposing mating elements and the opposing planar surfaces are configured to restrict movement of the bone screw within the housing along a single plane.

6. The bone anchor of claim 1, wherein the bore of the housing includes a lower portion comprising a spherical surface configured to mate with the spherical body when the bone screw is inserted into the housing.

7. The bone anchor of claim 1, wherein the retainer assembly includes an insert positionable within the housing and configured to engage a portion of the head of the bone screw when the insert and the bone screw are inserted into the housing.

8. The bone anchor of claim 7, wherein the retainer assembly includes a retaining ring configured to secure the insert within the housing.

9. The bone anchor of claim 8, wherein the retainer assembly includes a bias member positionable between the retaining ring and an annular lower lip portion of the insert to bias the insert against the head of the bone screw.

10. A bone anchor comprising:
  a bone screw including a head and a shank extending from the head along a longitudinal axis of the bone anchor, the head including a spherical body comprising opposing planar surfaces, each planar surface of the opposing planar surfaces including an extension defining a posteriorly facing lip terminating at first and second notches; and
  a U-shaped housing including a bore to receive the bone screw, the bore including opposing anteriorly facing mating elements extending inward from opposing sides along a lower portion of the bore, the opposing mating elements of the U-shaped housing configured to engage the opposing planar surfaces and the extension defining the posteriorly facing lip on each planar surface of the opposing planar surfaces, the spherical body permitting movement of the U-shaped housing relative to the head in a first plane and engagement of the opposing planar surfaces and opposing mating elements of the housing preventing movement of the head in a second plane orthogonal to the first plane and the first and second notches limiting rotation of the U-shaped housing relative to the head in the first plane.

11. The bone anchor of claim 10, wherein the posteriorly facing lip on each planar surface of the opposing planar surfaces projects over the corresponding planar surface of the opposing planar surfaces, wherein each of the opposing mating elements includes an upper surface configured to engage one of the posteriorly facing lips of one of the extensions when the bone screw is inserted into the U-shaped housing.

12. The bone anchor of claim 10, wherein each of the opposing mating elements includes a planar surface extending along the longitudinal axis of the bone anchor and wherein the posteriorly facing lip defines an undercut and faces a posterior end of the bone screw and an engaged portion of the one of the opposing mating elements faces an anterior end of the bone screw.

13. The bone anchor of claim 12, wherein each planar surface of the opposing planar surfaces of the head is adapted to engage one of the planar surfaces of the opposing mating elements when the bone screw is inserted into the U-shaped housing.

14. The bone anchor of claim 10, wherein the opposing mating elements and the opposing planar surfaces are configured to restrict movement of the bone screw within the U-shaped housing along a single plane.

15. The bone anchor of claim 10, wherein the bore of the U-shaped housing includes a lower portion comprising a spherical surface configured to mate with the spherical body when the bone screw is inserted into the U-shaped housing.

16. The bone anchor of claim 10, further comprising a retainer assembly including an insert positionable within the U-shaped housing and configured to engage a portion of the head of the bone screw when the insert and the bone screw are inserted into the bore of the U-shaped housing.

17. The bone anchor of claim 16, wherein the retainer assembly includes a retaining ring configured to secure the insert within the U-shaped housing.

18. The bone anchor of claim 17, wherein the retainer assembly includes a bias member positionable between the retaining ring and an annular lower lip portion of the insert to bias the insert against the head of the bone screw.

19. A uniplanar pedicle screw bone anchor assembly comprising:
　　a housing including a bore extending through the housing to a lower opening and including opposing mating elements extending inward from opposing sides of the bore adjacent the lower opening; and
　　a bone screw insertable into the housing and including a head and a shank extending from the head along a longitudinal axis of the bone screw, the head including a spherical body comprising opposing planar surfaces, each planar surface of the opposing planar surfaces including an extension defining a posteriorly facing curved lip overhanging the planar surface and adapted to engage a portion of a mating element of the opposing mating elements,
　　wherein after the bone screw is inserted into the housing the opposing mating elements and the opposing planar surfaces operate to restrict movement of the bone screw relative to the housing to a single plane and prevent movement of the bone screw relative to the housing in a plane orthogonal to the single plane.

20. The uniplanar pedicle screw bone anchor assembly of claim 19, wherein the posteriorly facing curved lip defines an undercut and an engaged portion of the one of the opposing mating elements faces an anterior end of the bone screw.

* * * * *